United States Patent
Vilser

(10) Patent No.: US 6,621,917 B1
(45) Date of Patent: Sep. 16, 2003

(54) DEVICE AND METHOD FOR EXAMINING BIOLOGICAL VESSELS

(75) Inventor: Walthard Vilser, Weimar (DE)

(73) Assignee: Imedos Intelligente Optische Systeme Der Medizin-Und Messtechnik GmbH, Weimar (DE)

( * ) Notice: Subject to any disclaimer, the term of this patent is extended or adjusted under 35 U.S.C. 154(b) by 0 days.

(21) Appl. No.: 09/117,236

(22) PCT Filed: Nov. 11, 1997

(86) PCT No.: PCT/DE97/02634
§ 371 (c)(1),
(2), (4) Date: Jul. 24, 1998

(87) PCT Pub. No.: WO98/23202
PCT Pub. Date: Jun. 4, 1998

(30) Foreign Application Priority Data

Nov. 26, 1996 (DE) .......................................... 196 48 935

(51) Int. Cl.[7] ................................................ G06K 9/00
(52) U.S. Cl. ......................... 382/128; 128/922; 356/39
(58) Field of Search ............................... 382/128, 100; 128/922; 356/39; 377/10; 707/104.1; 702/128; 606/5; 600/449, 443, 405, 439; 436/172; 351/212

(56) References Cited

U.S. PATENT DOCUMENTS

| 5,031,632 A | | 7/1991 | Watanabe | |
|---|---|---|---|---|
| 5,058,596 A | * | 10/1991 | Makino et al. | 128/665 |
| 5,090,416 A | * | 2/1992 | Ogino et al. | 128/691 |
| 5,186,173 A | * | 2/1993 | Zukerman | 128/663 |
| 5,240,006 A | | 8/1993 | Fujii et al. | |
| 5,549,597 A | * | 8/1996 | Shimmick et al. | 606/5 |
| 5,731,994 A | * | 3/1998 | Okubo et al. | 702/128 |
| 5,776,060 A | * | 7/1998 | Smith et al. | 600/340 |
| 5,777,340 A | * | 7/1998 | Ueno | 250/458 |
| 5,784,162 A | * | 7/1998 | Cabib et al. | 356/346 |
| 5,822,446 A | * | 10/1998 | Kato | 382/128 |
| 5,960,443 A | * | 9/1999 | Young et al. | 707/104.1 |
| 5,993,001 A | * | 11/1999 | Bursell et al. | 351/212 |

(List continued on next page.)

FOREIGN PATENT DOCUMENTS

| DE | 43 26 716 | 3/1994 |
|---|---|---|
| DE | 38 39 272 | 6/1995 |
| EP | 0 392 743 | 10/1990 |
| JP | XP-002061912 | 9/1987 |
| JP | XP-002061910 | 3/1988 |
| JP | XP-002061909 | 5/1995 |
| JP | XP-002061911 | 2/1996 |

OTHER PUBLICATIONS

Suzuki, Direct measurment of retinal vessel diameter; survey of ophthalmology vol. 39, 1995, p. 56–65.*
Delori, Noninvasive technique for oximetry of blood in retinal vessels, 1998, Applied optics, vol. 27, pp. 1113–1125.*
F.C. Delori, "Noninvasive Technique for Oximetry of Blood in Retinal Vessels", vol. 27, No. 6, Mar. 15, 1998.
Münch et al, "Adaptive Algorithmen Zur Automatischen Messung Retinaler Gefässdurchmesser", Biomed. Technik 40, 1995, pp. 322–325.
Mustererkennung 1994, Erkennen Und Lernen, 16 DAGM Symposium Und 18 Workshop Der Öagm, Herausgegeben Von Walter G. Kropatsch Und Horst Bischof.

*Primary Examiner*—Bhavesh M. Mehta
*Assistant Examiner*—Barry Choobin
(74) *Attorney, Agent, or Firm*—Jordan and Hamburg LLP

(57) ABSTRACT

The present invention pertains to a device for examining biological vessels, especially retinal vessels, including an evaluation unit in the form of an image manipulator (BM) enabling at least partial digitalization or isolation of a measurement window, whereby at least one vessel segment is represented by an electronic picture or picture sequence, which is then transferred to said evaluation unit.

93 Claims, 14 Drawing Sheets

U.S. PATENT DOCUMENTS

| | | | | |
|---|---|---|---|---|
| 6,000,799 A | * | 12/1999 | Van De Velde | 351/205 |
| 6,047,080 A | * | 4/2000 | Chen et al. | 382/128 |
| 6,048,314 A | * | 4/2000 | Nikom | 600/443 |
| 6,048,317 A | * | 4/2000 | Langguth | 600/449 |
| 6,110,110 A | * | 8/2000 | Dublin et al. | 600/405 |
| 6,198,532 B1 | * | 3/2001 | Cabib et al. | 356/346 |
| 6,527,718 B1 | * | 3/2003 | Connor et al. | 600/439 |
| 6,530,917 B1 | * | 3/2003 | Seiler et al. | 606/5 |
| 2002/0154271 A1 | * | 10/2002 | Donitzky et al. | 351/212 |

* cited by examiner

S2 AND S3 WITH PUPILLA LOCATIONS

PUPILLA LOCATIONS IN p IN THE EYE

S1 WITH PUPILLA POSITIONS

MEASUREMENT WINDOW POSITIONS
AT RELATIVE TIME RZ1, RZ2 x, o, - AVERAGE VALUES
FROM MEASUREMENT WINDOW

MEASUREMENT WINDOW LOCATIONS
AT RELATIVE TIME RZ1, RZ2

DEVICE AND METHOD FOR EXAMINING BIOLOGICAL VESSELS

BACKGROUND OF THE INVENTION

The invention pertains to a device for the investigation of biological vessels, preferably of retinal vessels, in which at least one vessel section is present as an electronic image or as a series of electronic images, said image(s) being supplied from a photoelectric receiving device to an evaluation unit. The invention can be applied for functional diagnosis and analysis of all optically accessible blood vessels, or vessels that can be imaged by other means. Preferably it is used for the examination of vessel behavior of the large retinal vessels. However, it can also be used for the examination of vessels of the iris, the conjunctiva and also of vessels which are optically accessible with a microscope or endoscope or by other means. In particular, vessels which are exposed during an operation, can be monitored and examined by means of a surgical microscope. The application of the invention is possible both to human blood vessels and also for the examination of animals. The imaging of vessels can take place by means of optical imaging systems with optical-electronic image conversion, or by means of electronic image generating systems, e.g., scanning of photographic vessel images. Its application is not restricted solely to the examination of vessels in the microcirculation, but rather it can also be employed in a favorable manner for large images of vessel sections created by means of ultrasound and other imaging principles. In the state of the art for examination of vessels, dilatation measurements of vessels in the back of the eye are known. These methods are based on the use of optical, precision measurement techniques in an ophthalmoscopic image, the use of precision optical measurement techniques and densitometry of the photographic negative or are based on photoelectric measurement methods.

According to DE 3,839,272 an apparatus is known for measuring the background of the eye, which is suitable for clinical purposes and which allows a measurement of dilated vessels, whereby the objective acquisition of tiny, pulsating, auto-regulative or local-regulative changes in vessel dilation is possible. In this case one image field with vessels of the eye background is imaged on at least two CCD line segments, whereby means are provided to change the image position and optical properties of the image. The apparatus can be operated in continuous mode or in flash mode. Likewise, the Suzuki, Y. (Surv. Ophthalmol. 1995, May; 39 Suppl. 1: 57–65) measurement station works with a CCD line. The disadvantages of the mentioned designs consist in that only quasi-continuous measurements are possible with single CCD lines, and with somewhat improved reproducibility compared to the state of the art, but still only with large systematic errors between the seatings and over the course of examinations. Clinically relevant, meaningful information is only obtained as a group average. The complex behavior of the vessels, including also the disclosure of free, local regulative vessel responses and pulsatory changes, are not reliable in a particular case and usually are not even detectable.

Various devices or methods are described to acquire the pulse shape of the retina vessels through the use of pulse-synchronous TV images or photographic images. For studies of this type, through the additional acquisition of pulse signals, the image recordings or digitizing can be controlled synchronous with the pulse. In this regard a device and a method are described in U.S. Pat. No. 5,031,632 with which the pulse shape of only one site of a vessel can be determined on-line from a pulse-synchronous TV image sequence. However, the proposed solution has a fundamental, exceptionally large measurement uncertainty which will not allow a clinically relevant, individual acquisition of the pulse shape of retinal vessel diameter. The disclosed pulse shapes do not correspond to the actual pulse shapes, as are measurable based on the diameter of the retina vessel.

A similar method is described by Dumskyi et al. (1996 Curr Eye Res. 1996 June; 15(6); 652–632). These methods do not have on-line capability, are very time-consuming and too inaccurate and likewise are of value only for statements about a group average.

Another photoelectric method was presented by Delori (Applied Optics Vol. 27, No 6,1988, 1113–1125), in which the vessel diameter is also determined. The measurement principle differs fundamentally from the proposed solution to be described below. A small, gap-like measuring surface scans under different color, extremely narrow-band illumination at one site of the vessel perpendicular to the vessel run across the vessel diameter and the resultant brightness profiles are location-corrected and combined into a summary profile, from which then the vessel diameter is calculated from the very error-laden half-value width of the edges. Large systematic error sources, in particular due to movements of the eye—which cannot be corrected entirely with the stated principle—in particular eye motions during the scan process—which cannot be corrected at all—affect the measured result. In principle, the measuring system can provide only quasi-continuous measured values with measurement times of about 1.6 to 3 s.

Sometimes tests are described in the literature for use of standard methods of image processing or complicated mathematic algorithms for acquiring the diameter of the retinal vessels. For example, Schack et al. (Mustererkennung 1994, Springer-Pub., 475–481) describe special adaptive methods, but they do not allow the required accuracy nor do they have on-line capability, even though the mathematic principles are initially much more promising than the known and unsuitable standard method of image processing for edge recognition.

With previously known methods and devices, the reproducibility between the sittings has a very low accuracy. This reproducibility is not suitable for the significant detection of regulatory parameters and pathological and therapeutic changes of an individual vessel of a patient. Regulatory changes and also physiological rhythms of stochastic changes of vessel diameter exhibit differences of less than 10%, sometimes only 1 to 2%, and are not individually and significantly detectable with the known methods. The previous methods usually do not have on-line capability and/or do not have sufficient time resolution and/or are not practical for clinical use. The invention is based on the problem of defining a method and a corresponding device for the examination of vessels with which the complex vessel behavior can be determined.

SUMMARY OF THE INVENTION

According to this invention, the problem is solved by a device and by a method having the properties stated in the patent claims.

The invention is characterized by a number of advantages.

The invention creates the technical prerequisites for the continuous measurement of the vessel diameter in association with the quasi-simultaneous or precisely simultaneous acquisition of the temporal and local dependencies and their changes. Thus the biological variability formerly interpreted as a source of error, e.g., vasomotion, blood pressure waves and local changes in lumen, are determinable and clinically evaluable. Now surprisingly, physiological effects such as the Bayliss effect, Meyer waves, vasomotions, vessel changes related to location, po2- and pco2-changes can now be detected individually for single vessel sections and persons, but also in addition their temporal and local profile can be recorded along a vessel. Accordingly, we obtain an entirely new quality of examination of vessels in the microcirculation.

The invention makes possible not only the simultaneous, on-line acquisition of location-dependent and time-dependent variables, but also the simultaneous, on-line acquisition of several vessels.

The invention reduces the systematic error in measurements considerably, tangibly improves the reproducibility and makes possible the highly significant detection of pathologic, therapeutic or provoked changes in single sections of a vessel, individually for specific persons and thus for the first time creates the prerequisites for optimized, individual therapy from the viewpoint of vessel behavior.

The invention makes use of the potential for data acquisition and effective evaluation of a number of beneficial and new diagnostic methods for the evaluation of vessel behavior and is not restricted to the retina vessels.

Furthermore, the application of the invention makes it possible to form powerful parameters for formerly non-measurable retina vessels which can be displayed in a graphically concise manner and now allows for the first time, an evaluation of a number of measured values.

The special types of presentation are tailored to the specific bits of information, in particular the subsequent allocation of measured data obtained from the image, back into the correct image.

In addition, the invention makes it possible to obtain parameters from a spectral analysis of the vessel diameter.

Furthermore, it is helpful that the method has on-line capability using low-cost PC equipment due to the invented configuration.

An additional, important advantage consists in that the device according to this invention consists of various, special apparatus which can also be employed individually. Some of the most important ones are:

- A fixation device according to the invention, with consistent fixation coordinates relative to the object space in the background of the eye, so that comparable measured results will be assured,
- The placement of one or more help windows to reduce the influence of motions of the eye, and
- the use of a measurement field so that the light stress on the eye is reduced.

The invented method and the invented apparatus allow a number of different implementations with different clinical findings to problem constellations which are of equal clinical relevance. As photoelectric receiver units, we can use both digital or analog recording systems for image sequences, and also imaging systems, such as laser scanner systems and conventional, optical imaging systems with optical-electronic imaging or any other systems that can supply an electronic image of a vessel section, so that the number of possible designs of the invention will be expanded even more.

The invention will be explained in greater detail below based on one design example. In this regard we will explain a measuring station for on-line examining of near-papilla retinal branch vessel sections. The clinical background is the question of the degree of local regulation and a search for the causes of limited local regulation pertaining to vasomotion or contractility function and vessel wall stiffness along the vessel sections. These clinical questions cannot be examined by any of the known methods.

DESCRIPTION OF THE EMBODIMENTS

Figure 1:
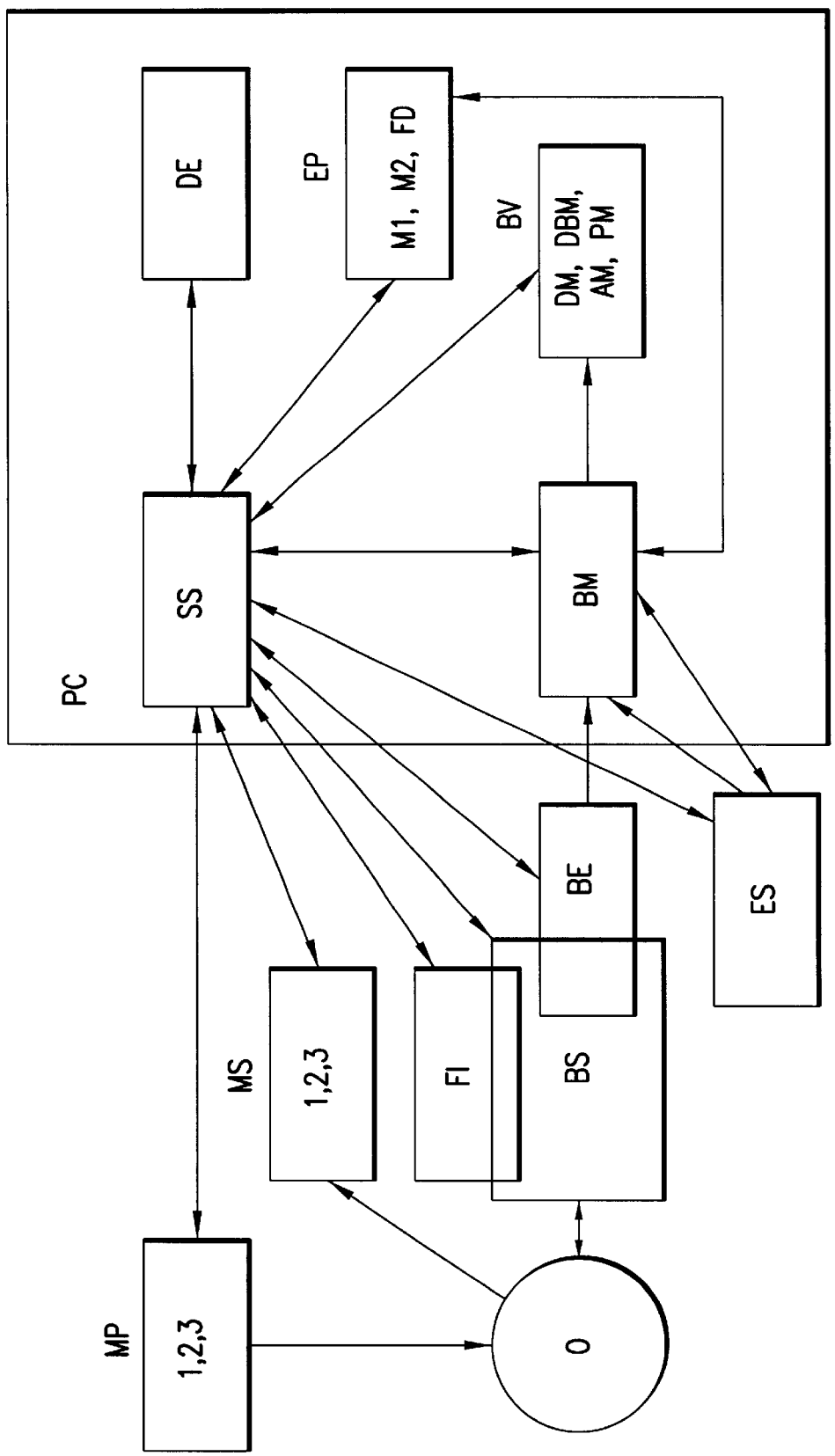
FIG. 1 A block diagram of the overall device.

FIG. 1 explains the overall arrangement of the device. Objects O are preferably the large, retinal branch vessels of the living, human eye and the object space is defined as the background of the eye. The foveola is defined as the reference point of the object space. As video source, the invention employs an imaging system BS in the form of a lighting-modified, retinal camera (to be described below), with a new combined inner and outer fixation device FI (also described below) and a CCD image sensor as image receiver BE. The imaging system BS is used for lighting and optical imaging of the needed fundus section with the vessel sections to be examined. The image receiver BE is used for optical-electronic image conversion into a preferably continuous TV image sequence.

The analog video signals of the image sequence coming from the image receiver BE are supplied to an image manipulator BM. The image manipulator BM, for example, a frame grabber, is equipped with means to create the image window and the associated time window of the invention (to be explained below) and to digitize the window contents within the time window and pass them to the signal-processing unit BV. The geometry and position of the image windows, and the measuring and recording times of the time windows, and their sequence are variable from image to image adapted to the measuring process. In the image manipulator unit there are also means to display the video image on an adjustable monitor EP, means to display the current window and window positions in the fundus image of the monitor, and means for identifying the video images on the monitor, preferably with the date, the reference time and an identification number for the current examination IDU. The adjustable monitor M1 is one means for presentation of results EP and is used for observation of the current results of the setting of the vessel sections under examination in the windows, in order to verify or correct the settings before and during the examination process.

The signal processing unit BV consists of memory and computing units, called the diameter module DM, which processes the digitized window contents according to a method to be described below, automatically recognizes vessel sections in the individual lines or columns, determines the vessel diameter correctly for the slant position, and sends this together with the vessel middle positions in the window, to the control unit. In addition, the signal processing unit consists of computing and memory media for evaluation of the measured results on the vessel diameter, the optional, supplemental measured data from the MS and the control data from SS, the saving of measured and evaluation results in association with the patient data—and control data for forming of characteristic quantities (evaluation module AM). Other provided features are used to calculate the presentation of results and compilation of measurement protocols (presentation module PM), whose data are sent via the control unit to the equipment in the evaluation unit (EP). In addition, the unit BV contains means to save and administer a database (database module DBM) in which the measurement, control, patient and evaluation data are saved in the preferred format to be described below and compiled for additional use and to send the data to the evaluation or presentation modules. The stated modules feature preferably their own processors. The diameter module can be constructed as a multiprocessor system to increase the processing speed. Another hardware implementation of the stated modules can be designed in whole or in part using Risk engineering.

The control unit SS consists of memory and computing units to implement the sequence control (to be described below) of the invented method and it also consists of means to implement, drive and poll the interfaces to the input units for the dialog mode (DE) for the optional measuring systems MS, for the optional manipulation units, for the fixation unit (FI) for the CCD camera (BE) and for the imaging system BS. The control unit controls the entire measuring and evaluation process of the invented method to be described in greater detail below.

The unit DE includes input means for dialog mode, preferably mouse and keyboard.

Reference symbol EP standard for the adjusting monitor M1 mentioned above, and means for presentation of the results, preferably a PC monitor M2 and a color printer FD. The outputs from the system are presented on the PC monitor M2 to the examiner for dialog operation. Preferably an image memory controlled by the SS is included; this image memory records in whole or in part—and preferably in parallel to the measuring process—the image sequence supplied to the BM from the BE and at any time can replay this saved image sequence, instead of the image sequence of the BM coming from the BE, e.g., for display on the adjustable monitor or for evaluation. Means are provided in the video memory and in the SS so that in the case of an analog tape recording with a controllable video recorder, e.g., model AG 7355 with serial interface (Panasonic), the tape can be identified with a time code and a tape identification number, or in the case of digital image recorder, it can be identified as a minimum, with the reference time and an examination identifier (IDE) (see below) for each image. These means also makes it possible to use the full range of all known functions of a TV image memory, such as recording, search, rewind, fast forward, replay, etc. It makes no difference for the invention whether the image sequence is saved analog or digital. For the optional, parallel recording of images, the frame grabber has to be configured properly to handle the image recording and replay, including image identification or coding, and also for transfer or transmittal of the image sequences. These means make it possible to identify the image sequence coming from the BE, image by image (under control by the SS) and to provide them to the image memory for storage, and also in the case of replay of saved image sequences, it is possible to pick up and process saved image sequences instead of image sequences coming from the BE. The image coding takes place preferably image by image with the name, the date of examination (DU) and the reference time. It can be helpful to write other data into the image, which then have to be passed from the SS to the BM. In the case of optional usage of a video memory, the reference between the particular examination data and patient data will be produced in the database for the saved images or image sequences and their time reference.

The measuring and manipulation units MP/MS are optionally configured to correspond to the medical question at hand. But preferably, for all examinations means are provided for quasi-continuous measurement of blood pressure; but it should be determined preferably at intervals of 1 minute, at the minimum immediately before and after an examination process via SS and preferably systolic and diastolic blood pressure values should be taken under sequence control and then the values should be moved by the SS for storage, evaluation and presentation.

The modification of the retina camera according to this invention will be explained in greater detail below. The modification pertains to the installation of the invented fixation system, consisting of outer and inner fixation, the use of special measuring filters and additional means and modifications in the illuminated beam path, and also means to control the units of the illuminated beam path including the light sources. The modifications described below are not compulsory for the invention, excepting the use of the special filter, but rather represent merely favorable configurations that most prominently bring out the advantages of the invention.

Figure 2:
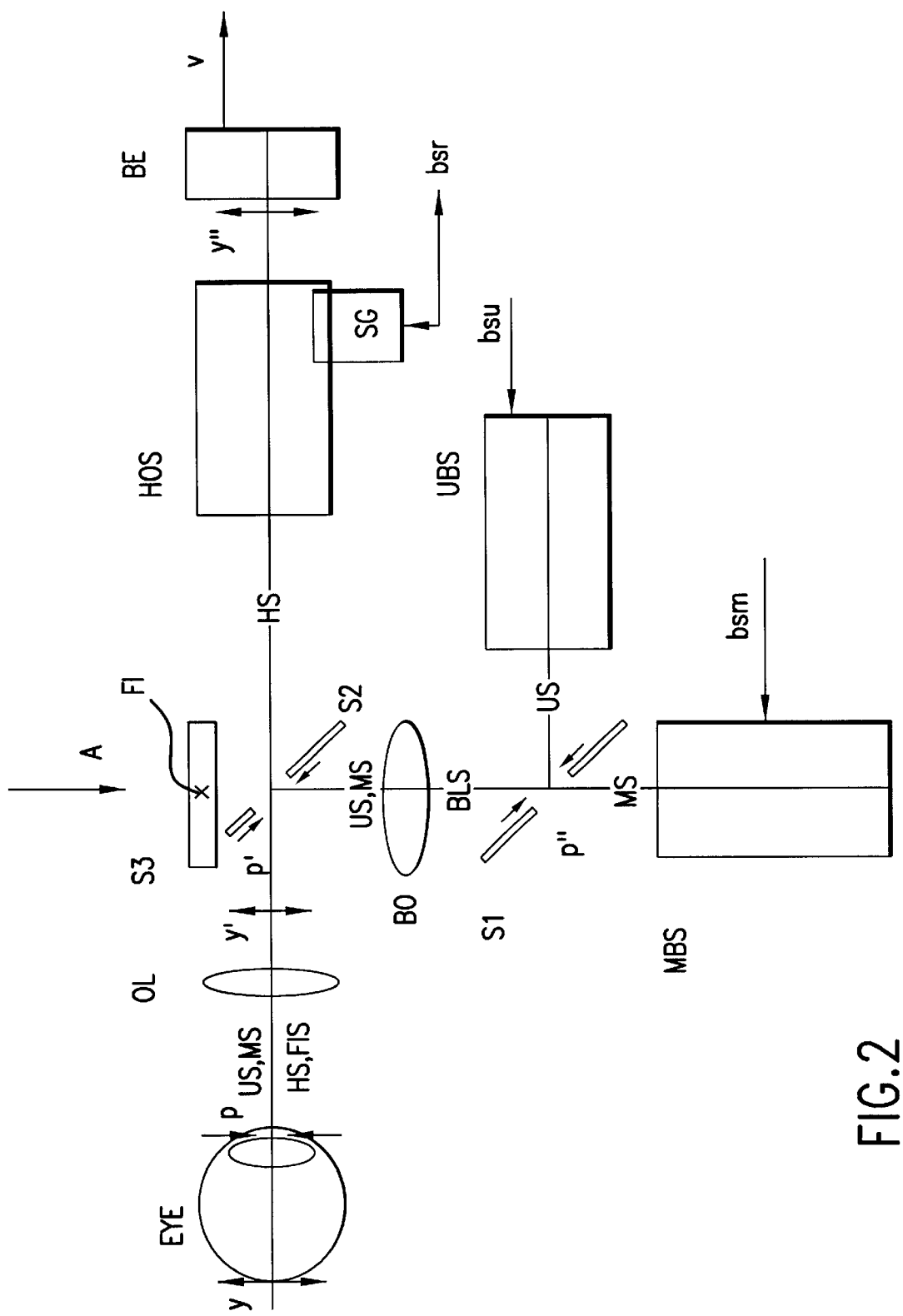
FIG. 2 A block diagram of the device described in the design example

The image-generating system BS is presented in detail in FIGS. 2 and 3. The Figures show two views aligned perpendicular to each other, and FIG. 3 presents a top view of the arrangement of FIG. 2 seen from direction A. It consists of an imaging, main beam path HS with the ophthalmoscope lens OL and the lens system HOS, a perimeter lighting beam path US with the perimeter lighting system UBS, a measured field lighting beam path MS with the measured field lighting system MBS and also the fixation beam path FS. The fixation beam path is divided by two mirrors S4$a$ and S4$b$ (FIG. 3) illustrated in FIG. 3$b$ into an outer fixation beam path FAS and an inner fixation beam path FIS, whereby in FIG. 2 only the inner fixation beam path is shown, which is reflected in the region of the illuminated pupilla plane via the mirror S3 into the main beam path. With respect to the illustrated view, it is moving from a vertical direction to the plane of the paper and then moves jointly and parallel with the main beam path HS and the illuminated beam paths US and MS via the ophthalmoscope lens OL into the eye. Perimeter lighting beam path US and measured field lighted beam path MS are used in this invention for mutually independent lighting of the background of the eye with a lighted measured field (to be described below) and a lighted perimeter. Both beam paths are combined by the mirror S1 to divide the pupilla in the lighted pupilla plane p" as illustrated in FIG. 9, and are reflected into the main beam path by the mirror S2. S2 and S1 are congruent to each other and in this example, they effect the division or combining of beam paths by means of pupilla division, i.e., that all lighted and imaging pupilla planes including that of the inner fixation beam path coincide in the region of mirrors S2 and S3 at p' and are congruent to the pupilla of the eye p. All beam paths run together via the ophthalmoscope lens OL and through the optical layers of the object (eye) and penetrate the object space with the sections of the retina vessel to be examined.

The imaging units of the main beam path are the optical layers of the eye, the ophthalmoscope lens OL and the optical system HOS which image the object plane y in the image plane y" on the sensor plane of the CCD receiver BE, and in this example they form an intermediate image plane at y'. In addition to the creation of a reflex-free image of vessel sections on the receiver plane of the CCD camera BE, the main beam path is used to focus the image (poor vision compensation) based on a known arrangement of known optical means in the beam path, which are combined together into the lens system HOS. The optical system HOS is equipped with a poor-vision compensation (not illustrated) which is controlled by the SS. This compensator is adjusted on the control element SG by the examiner based on the control image on the adjustable monitor M1, and the refraction value for the current poor vision is determined and is sent as a signal BSR to the control unit SS. The refraction value of the eye under examination can then be determined with respect to the Gullstrand eye focused at infinity, in a known manner due to the offset of the poor-vision compensation obtained by the bsr; this value is in a defined relation to the refraction value when the fundus image is sharply focused. In other design examples, the manual servoelements for operation of the poor vision compensator are designed as automatic servoelements and with means to control these servoelements, which determine, in a known manner, the focus state from the images of the eye background and form control signals for setting the focus. The driving of the servoelements is then performed by SS.

Figure 9B:
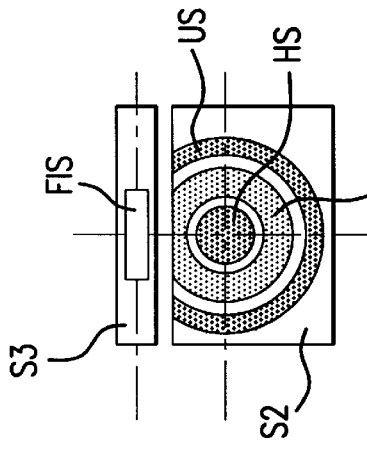
Figure 9C:
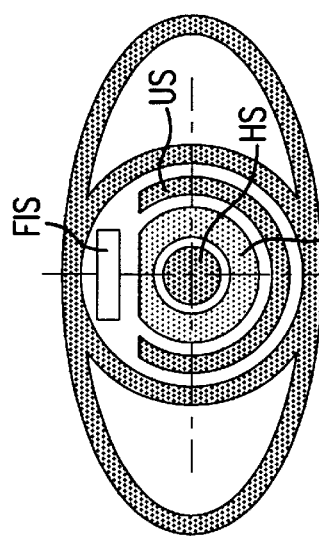
Figure 9A:
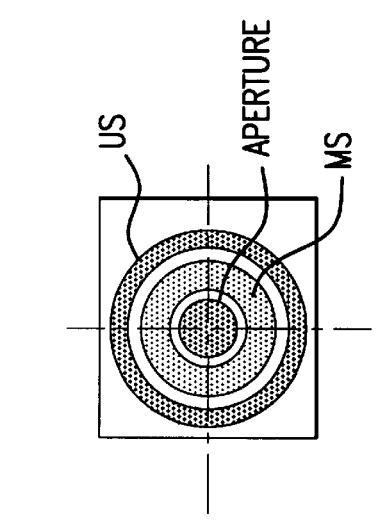

The perimeter illuminating beam path US is reflected into the measured illuminating beam path MS by means of perforated mirror S1 (in a plane preferably congruent to the illuminated pupilla) by means of geometric beam division so that the perimeter illuminated pupilla uses the outer beam region of the pupilla surface (see FIG. 9). FIG. 9a shows the pupilla position of US and MS on S1. FIG. 9b presents the pupilla positions of all beam paths on mirror S2 and S3 opposite the viewing direction A. FIG. 9c shows the pupilla position of all beam paths in the eye. The lighted lens unit BO is used for intermediate imaging of the pupilla position of the illuminated beam paths in p' and of the perimeter illuminated field, and also of the measured lighted field on the background of the eye. Preferably the beam space in the pupilla region p" for imaging of the measured lighting field and perimeter lighting field goes to infinity.

Figure 10:
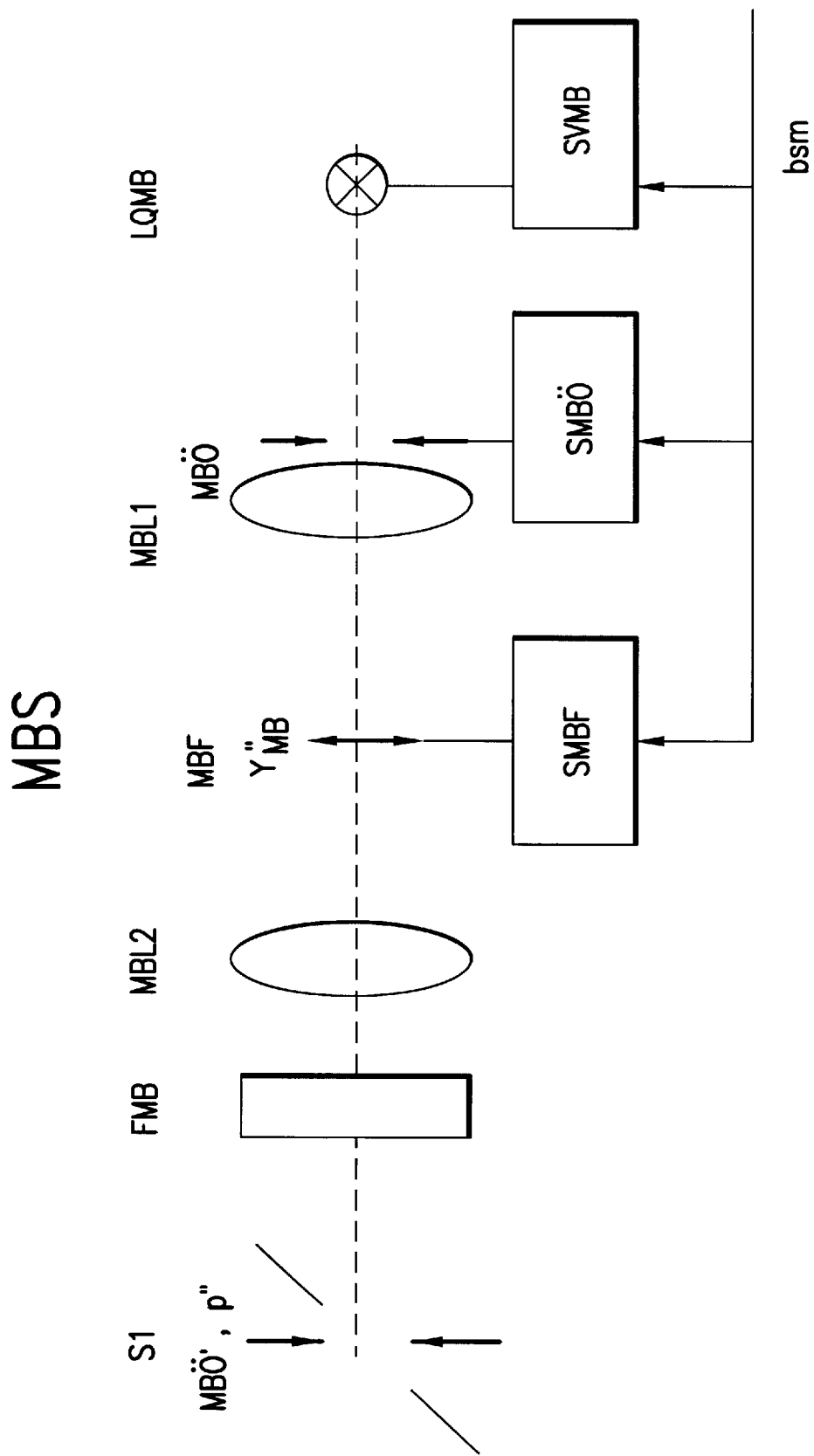

The measured field illuminating system MBS together with the lighting lens BO, the ophthalmoscope lens OL and the layers of the eye, jointly produce a bright lighting in the object plane at the background of the eye and a very sharply delimited measurement field. The measuring field presented in FIG. 4 has a lighted surface at the background of the eye; this surface has a controllable geometry and position and the measurements take place therein. The brightness and spectral composition of the light needed for the measurements is handled on this surface. The cooperation of measured field and the viewed, measurement window will be discussed below together with a description of the invented method. The lighting system MBS preferred for this design example is presented in FIG. 10. A halogen lamp LQMB powered by a controllable lamp power supply SVMB sends light through the open aperture MBO and the lens system MBL1 to the measurement field aperture MBF. The lens system MBL2 focuses the measurement field aperture MBF to infinity and the open aperture MBO is focused to the pupilla plane p", where the perforated mirror S1 is found. In the parallel beam path there is a bandpass filter MFB with a spectral characteristic defined below. The lighted measurement field is designed preferably as a gap. With the adjusting unit SMBF there are means for independent adjustment of gap height and width and of the position of the gap to the middle of the image field; the adjustments can be made in two mutually perpendicular coordinates and in the direction of the optical axis. Thus the gap image at the fundus can be adjusted to any vessel section with any desired surface area of the particular vessel sections. The gap motion in the direction of the optical axis makes possible a focusing of the measured field lighting onto the background of the eye according to the determined poor vision value from the bsr signals. In the lamp power supply SVMB there are means to control the lamp current. The opening aperture MBO is configured so that it produces the pupilla image presented in FIG. 9. The signals needed for automatic control of all described settings of the measured field lighting system MBS are jointly called the lighted measurement field coordinates bsm.

Figure 11:
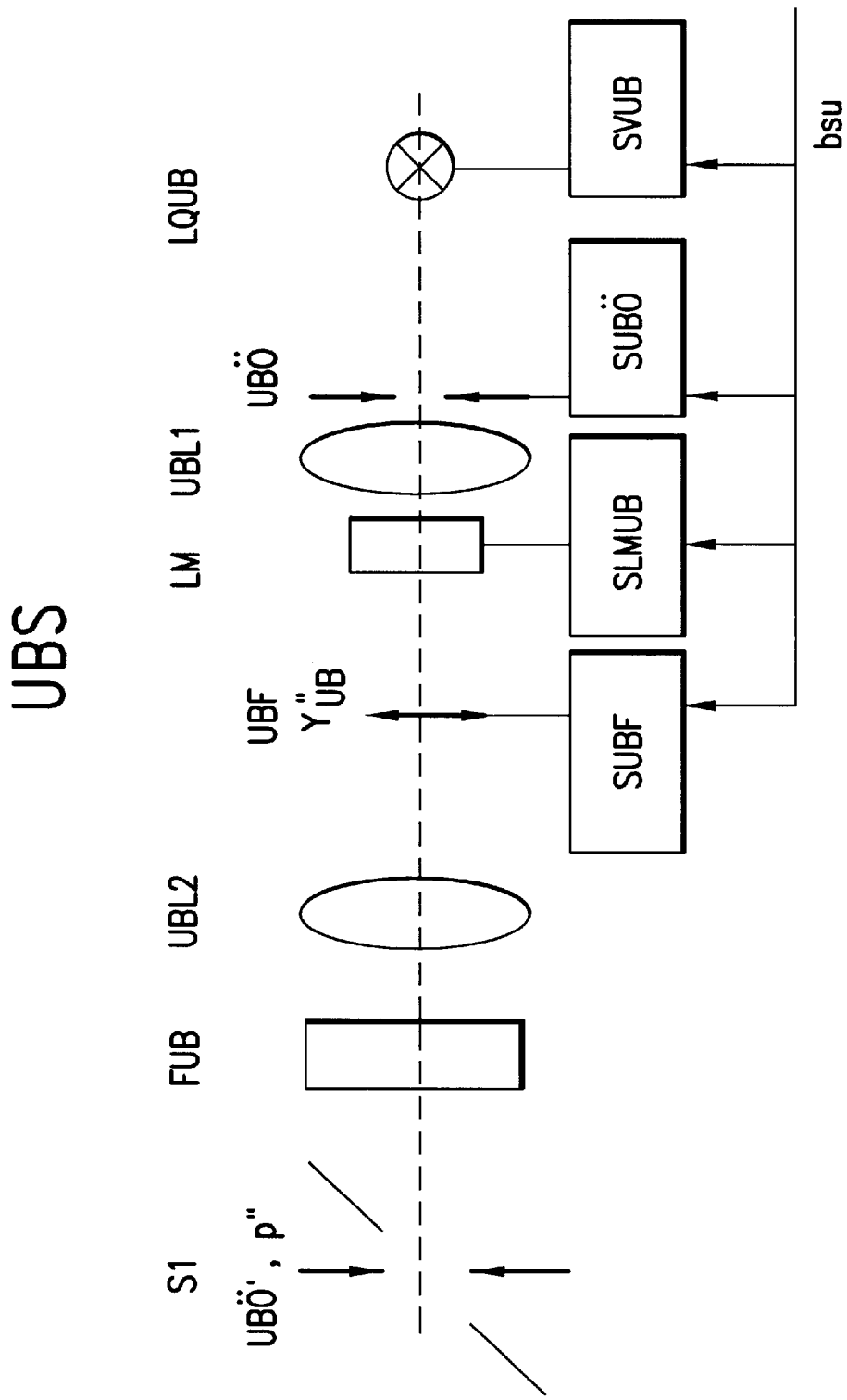

The perimeter illuminating system UBS together with the imaging system BS, the ophthalmoscope lens OL and the optical layers of the eye are used jointly to light up the background of the eye. This lighting is used for an overview when adjusting the background of the eye and can also be used according to this invention, for light provocation of the retina vessels. Independently of the setting of the measured field lighting, the brightness, geometry, position at the background of the eye, and spectral light composition of the perimeter field lighting can all be separately adjusted. For example, any particular light stimulus can be fired at these coordinates into the retina and the response of the vessels can be analyzed. The cooperation of perimeter lighting and the observation-side measurement window will be discussed with the description of the method presented below. The design example of the perimeter illuminating system selected for this description is described in FIG. 11 and discussed in greater detail below.

A halogen lamp LQUB powered by a controllable lamp power supply SVUB sends light via the open aperture UBO to the light modulator LMUB and to the perimeter aperture UBF via the lens system UBL1. The lens system UBL2 focusses the perimeter aperture UBF to infinity and the open aperature UBO to the pupilla plane p", where the perforated mirror S1 is located. In the parallel beam path there is a bandpass filter FUB for this design example; preferably it has the spectral characteristic defined in the claims. The lighting-side perimeter aperture is designed as an adjustable iris aperture. This adjusting unit UMBF is a means for adjusting the aperture diameter and the position of the iris aperture in the direction of the optical axis. The iris aperture movement in the direction of the optical axis allows adjustment of focus of the perimeter lighting on the background of the eye corresponding to the determined poor vision value from the bsr signals.

In the lamp power supply unit SVUB there are means to control the lamp current. The opening aperture UBO is configured so that it produces the pupilla image of the perimeter beam path illustrated in FIG. 9. The light manipulator unit LMUB is a switch to cover the opening of the open aperature and thus to modulate the perimeter lighting which is driven by the SLMMB unit. The signals needed for automatic control of all described settings of the perimeter lighting system MBS are together called the light-side measured field coordinates bsu.

Figures 3A, 3B:
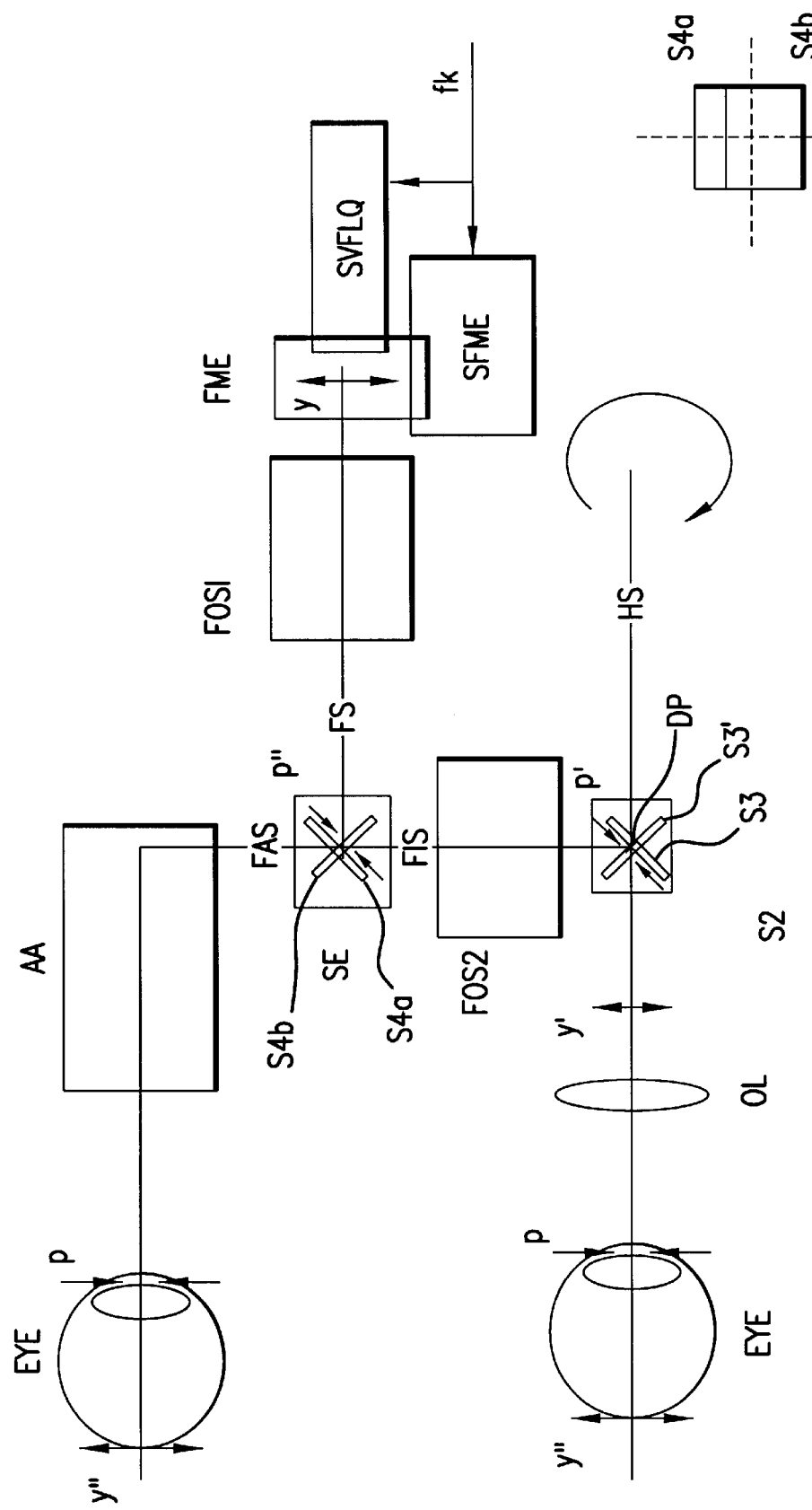
FIG. 3 A block diagram of the device described in the design example; a second view shown here FIG. 4 The presentation of an image field with windows FIG. 5 A block diagram of the process sequence FIG. 6 A sample presentation of a functional image FIG. 7 A sample presentation for a time display FIG. 8 A sample presentation for the vessel run FIG. 9 Mirror and pupilla positions in the mirror plane S1/S2/S3, FIG. 10 The design example of the MSB, FIG. 11 The design example of the USB, FIG. 12 A representation of the formation of the primary data string for the vessel diameter on a scanned, measurement surface, FIG. 13 A representation of the formation of the primary data string for the vessel diameter in parallel acquisition of the local dependence, and FIG. 14 A representation of various arrangements of the scan region.

An optimum fixation of the eye to be examined is an essential prerequisite for optimum results. The best fixation is an inner fixation, i.e., the fixation mark is offered to the eye under examination. The limits of this method are that the fundus sections that can be reached with the image field are bounded on the periphery and in certain cases the examined eye cannot see the fixation mark. Therefore it is more usual to use the outer fixation in which a lighted fixation mark moving in space is offered to the non-examined eye at a distance from the neighboring eye. Various modifications of this inner and outer fixation are currently underway in an attempt to eliminate the disadvantages of the standard fixation devices. For example, means for focusing the fixation mark are used and/or flashing fixation marks are used and/or arrays of light emitting diodes have been proposed with defined, adjustable fixation marks used in space for outer fixation. However, the previous methods have one important disadvantage which consists in that they do not afford automatic and sufficiently reproducible adjustment of fixation coordinates independently of the type of fixation (external or inner fixation). The device according to this invention used for fixation as a modification of the retina camera has several advantages. It allows simultaneous inner and outer fixation and is intended to eliminate these disadvantages and at the same time, it has the advantage of automatic setting of the fixation coordinates. The essential consideration according to this invention, is the consistent coordinate basis in object space, i.e., the angular setting of the examined eye and of the neighboring eye must be precisely the same under the same fixation coordinates, regardless of the use of outer or inner fixation. The invented solution handles this requirement by means of parallelity of the main optical axes of the main beam path with that of the outer and inner fixation beam path. FIG. 3 presents one design example of this. The imaging system BS is illustrated with an integrated fixation device in a perpendicular view viz FIG. 2. Both eyes of the patient can be seen, whereby the eye to be examined is identified by the main beam path HS penetrating into the eye. The main beam path HS is illustrated with its main optical axis. The fixation mark FME is focused to infinity via the optical system FOS1. The mirror unit S4 splits the common fixation beam path FS into the outer fixation beam path FAS and the inner fixation beam path. This mirror unit contains either a mirror tippable by 90°, or as in the design example, two mirrors tippable by 90° to each other, each of which represents an aperture for the two beam paths FIS and FAS as illustrated in FIG. 3b. The mirror S4a is imaged by means of optical system FOS2 as a pupilla image of FIS in the pupilla plane of the main beam path and reflects FIX parallel to the main beam path in the direction of the eye being examined. In this case the fixation mark is imaged in the image plane y'. The mirror S4b is focused via the optical system AA into the eye pupilla of the neighboring eye, whereby the optical system AA again focuses the fixation mark FME coming from infinity back into infinity, and contains means (not illustrated) for correction of the different poor vision between the two eyes for setting of the focus of the fixation mark for the neighboring eye. In addition, known means (not illustrated) for adjusting of FAS to the eye spacing are provided, which do not change the parallelity of the optical axis of FIS and FAS to each other. As fixation mark a light emitting diode is used. The SFME is a feature for fine-tuning of the light emitting diode and when the movement of the fixation mark is sufficiently large, into the congruent image plane to the foveola. This is achieved by adjustment in the direction of the optical axis and in two perpendicular coordinates of the congruent image plane to the eye background, whereby the fixation coordinate axes coincide preferably with those of the CCD matrix and those of the lighting systems. The focus setting of the fixation mark for the examined eye takes place by settings based on the poor vision values already determined, from which the position of the plane congruent to the fundus is calculated in the fixation beam path and is adjusted by means of fixation coordinates and SFME.

The brightness of the light emitting diode is modulated by means of the power supply unit SVFLQ. The control signal obtains SVFLQ from the control unit SS. The fixation control coordinates for the motion of the light emitting diodes and their brightness are combined under the reference FK and are made available by the control unit.

FIG. 3 presents the right eye as the eye to be examined. In case the left eye is to be examined, then the main beam path will be adjusted to the left eye. In this case, the fixation system must be positioned as the mirror image of the main axis. Mechanical means are provided to turn this reflection by rotation of the entire fixation system by 180° about the main axis HS, associated with the tipping of the mirror from a setting S3 by 90° against the rotation point DP into the setting S3'. Now the azimuth ratios are exchanged just once, whereby means are provided for detection of the setting of the fixation system (right or left), which passes this setting to the control unit and it is taken into account for proper calculation of the fixation coordinates. Preferably the color of the fixation mark will be selected as red and a red-barrier filter is located directly in front of the CCD camera to block the fixation light.

The invented method will be explained in greater detail below based on the selected design example. The method with the described device makes possible the (preferably) on-line, but also off-line measurement and suitable display of the local dependence of vessel diameters along vessel sections to be examined and at the same time, the display is possible as a function of the time, and also it is possible to analyze the vessel behavior due to inclusion of provocation methods and/or to form and display of relevant parameters to describe the local and the temporal vessel behavior. Thus preferably the location-dependence will be determined over at least one vessel section of suitable length, preferably 1.5 mm length, at one and the same time interval, e.g., within one image. But this precise simultaneity is not required. The determination of the location-dependence along a vessel section can also take place in time sequence from one vessel section to the next, when the attainable accuracy is still sufficient for the biological or medical matter at hand.

Figure 4:
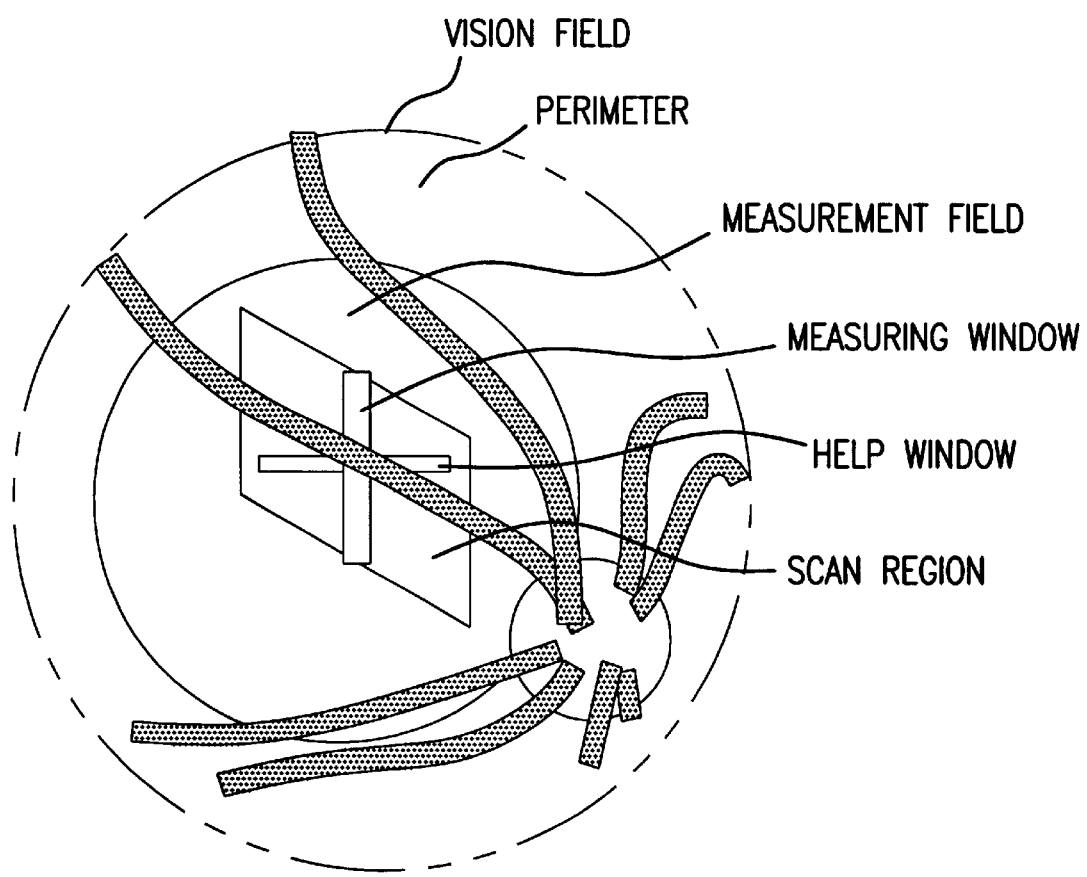

The examinating process takes place within the specified window. FIG. 4 presents the relationship between the image field, the measured and help windows, the perimeter lighting or provocation lighting and the measured field lighting. The perimeter lighting created by UBS is used during the setting of the vessel region to be examined for orientation to the background of the eye. The diameter of the perimeter lighting and lighting intensity is just strong enough that an orientation to the fundus is possible. Preferably the standard setting is such that the perimeter lighting will light up the entire image field, but the papilla and vessels are just barely discernible.

The measured field created by MBS is used for lighting of the measured window and help window. The measured window is an image region that is tailor cut and digitized by the image manipulator unit BM and sent to the data processing (DV) unit. That is the region in the vessel sections which is automatically recognized by the vessel diameter module and analyzed along the pixel lines and/or pixel columns, that is, all vessel diameters and the associated vessel middle positions of the vessel sections are recognized in the measured window and intersecting pizel lines and/or pixel columns are determined, output to the control unit and saved in the primary data matrix, allocated to relative time RZ, in which the current image was recorded. In this case, the slant-position of the vessel diameter has already been corrected in the diameter module, because the vessel direction will be sufficiently perpendicular to the measurement direction only in rare cases. If the vessel diameter is determined in the direction of the pixel columns, then the recording of the local dependence of the vessel diameter takes place along the vessel with perpendicular pixel line direction and vice-versa. Preferably according to the invention, the measuring direction and local dependence perpendicular to each other are determined in correspondence to the pixel lines and pixel columns. The width of the measured window in the measuring direction for the vessel diameter is preferably set large enough so that the vessel will intersect the measured window in spite of eye movements. Another advantage is that the measured window can intersect several vessels and the diameter module DM in this case will analyze or measure all vessel sections intersecting the measured surface in the manner described. Perpendicular to the measuring direction the number of pixels of the measured window should be at least large enough so that from the shift of the vessel middle in the measured window, the slant position will be determined and a value can be formed for correction of the slant position. The correction of the slant position takes place preferably while still in the diameter module. This measuring principle will then automatically produce the local dependence of the vessel diameter along the vessel perpendicular to the measuring direction for the vessel diameter, pixel column by pixel column, or pixel line by pixel line. The time dependence on the vessel diameter is produced in the primary matrix to be described below, when the measuring process is repeated image by image with increasing relative time from the beginning of measurement (reference time). When using the standard European TV cameras, the possible temporal resolution is then 40 ms. Only a few pixels perpendicular to the measured direction are needed for correction of the slant position. A few pixels in the direction of the vessel run are not sufficient for a relevant and medically evaluable, local dependence of the vessel diameters. In order to have a satisfactory determination of the local dependence, there are two preferred methods that will come into consideration.

In the first case, a column-like measuring window is used, depending on the position of the examined vessel in the image field, which horizontally intersects the vessel, or vertically intersects the vessel under examination as in the example of FIG. 4; this intersection is set by the examiner or occurs automatically. The column-like width of the measured window is selected preferably as 10 pixels, and the height of the measured window will be 100 pixels, for instance. The image by image control of window geometry and position using the control unit of this invention, is utilized for temporal changes to the position of the measuring window, which is itself moving stochastically of systematically within a scan region defined by the examiner.

Figures 12A, 12B:
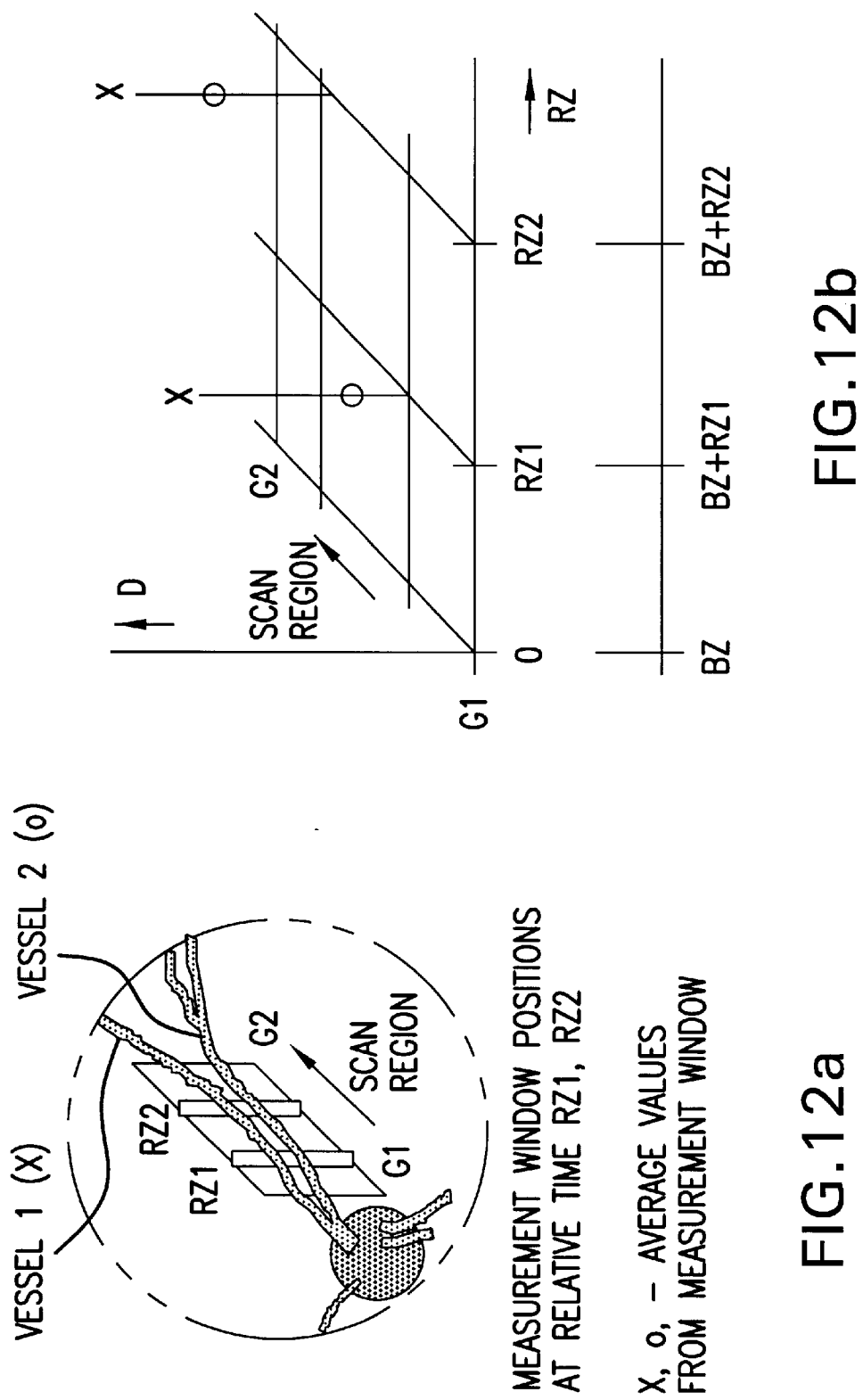

The examiner or the control matrix of a reference examination specifies the coordinates of the measuring window for the two outer boundary layers (G1 and G2) as indicated in FIG. 4, within which the measuring window migrates within one image or from image to image and senses the location along the vessel. This region is called the scan region. In this case, the diameter of the column-like measured surface, corrected for its slant position, is averaged across the width of the column and output. FIG. 12 shows the measuring process and the generation of the data stream of the primary matrix. FIG. 12a presents the image field against the background of the eye, as already known from FIG. 4, with the measuring window and the scan region. RZ1 and RZ2 are two time points which correspond to the two measured window positions entered in FIG. 12a. FIG. 12b represents the reference time axis proceeding from the reference time of the beginning of the examination BZ and also the data space from relative time RZ, scan site and vessel diameter for the two measured vessels 1 and 2.

Figure 13B:
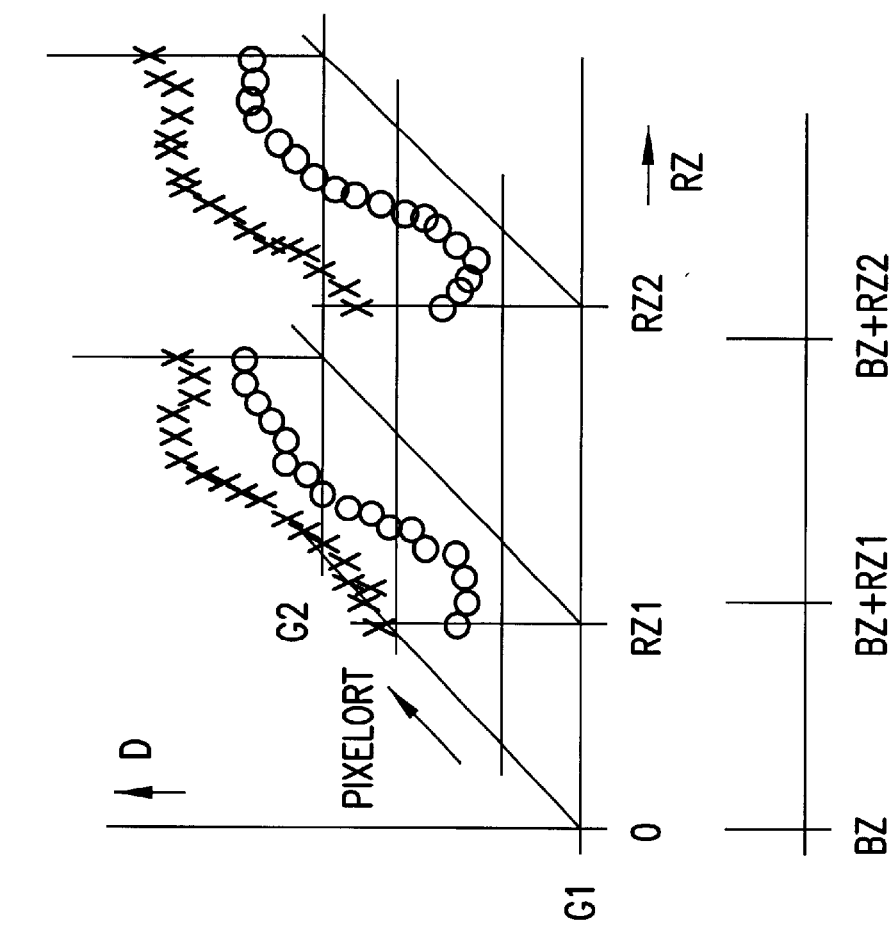
Figure 13A:
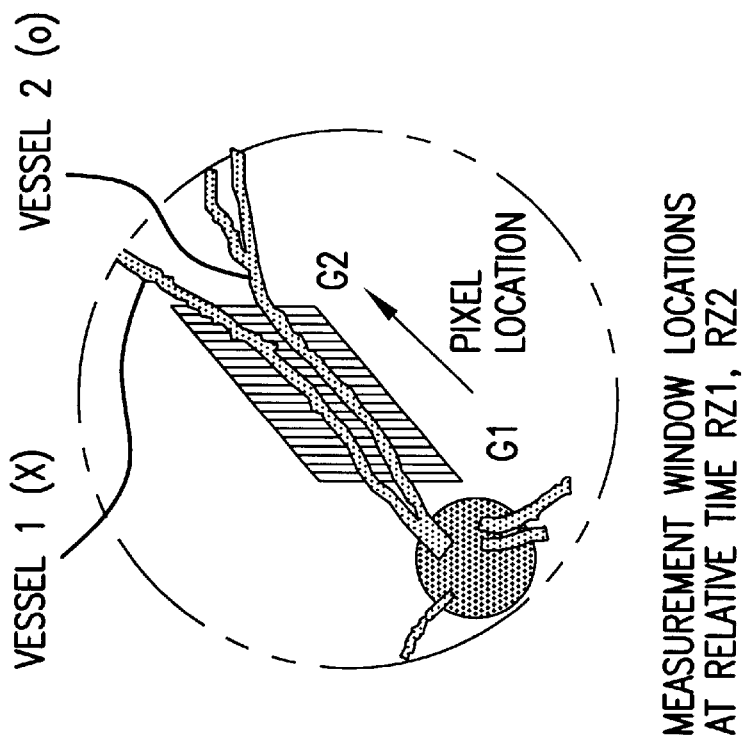
Figure 14A:
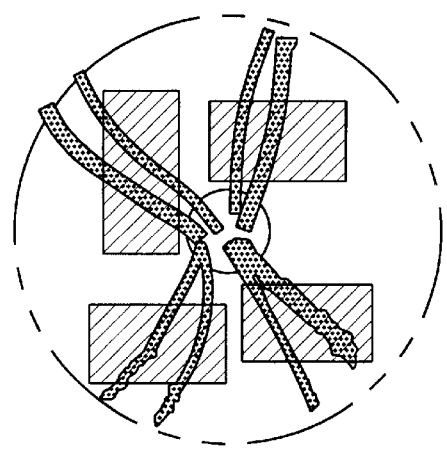
Figure 14B:
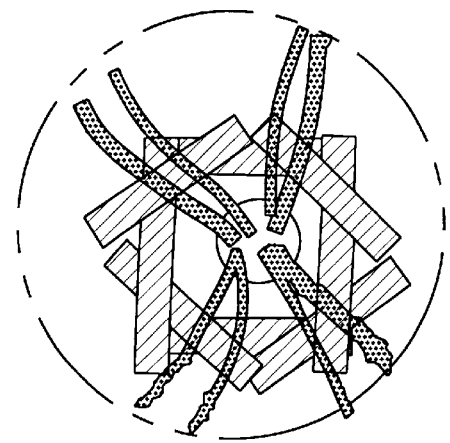
Figure 14C:
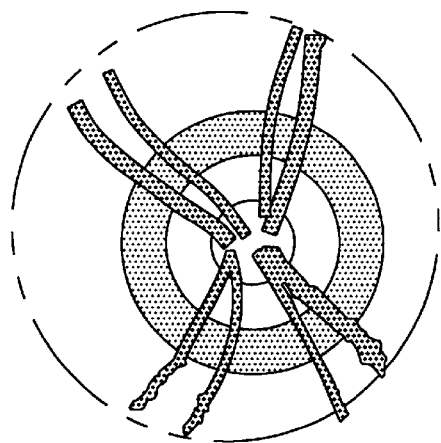

The advantage of this measuring method is the small required computation capacity for one measured surface and the potential to define a number of parallel measured surfaces in the image. Another design of the measuring method makes use of a broad measuring window which is defined, for example, by the examiner on the adjusting monitor in such a manner that the vessel sections to be examined will be sufficiently insensitive to motions of the eye. The measured surface remains unchanged in the image field over a longer sequence of images and as illustrated in FIG. 13, denotes the local dependence of the vessel diameter along the measured vessel sections within the measured window perpendicular to the measured direction parallel in time. This figure should be understood analogous to FIG. 12, where the coordinates of scan site are replaced by the pixel site. The minimum local resolution is then established by the line or column width. Preferably with a large computer power and favorable slant position of the vessel, the same measuring process can be performed on-line, image by image, in parallel when the measured direction of vessel diameter and local dependence are exchanged, and thus we obtain a greater accuracy and a better control of the correction of slant position.

The help windows are used to verify and correct the eye motions during the measuring process [and] the vessel sections can shift with respect to the measured window. This is negligible for components of eye motions in the measured direction of vessel diameter using a time resolution of 40 ms, but it is a problem for displacements from image to image along the vessels and leads to a large uncertainty of the measurement. The vessel diameter can change along the site by up to 10% and more, which is reflected in the reproducibility or in systematic errors.

Preferably two mutually perpendicular column-shaped help windows are defined in the direction of the pixel line and column. In the described, second case of wide measured surfaces, at least three pixel lines and three pixel columns from the middle of the first, defined measured window are additionally used as help windows. In the case of column-shaped measured surfaces, the control unit will create both help windows, likewise in the middle of the [word missing] consisting at least of 3 pixel lines and 3 pixel columns with preferably the same height as the measured window, which do not change their position from image to image. FIG. 4 shows only the horizontal help window, since the vertical window is covered by the measured window.

The vessel middles in the help window are determined in the help windows and compared with the set values from the first image. From these values, correction values are determined for the motion of the vessel sections from one image to the other and are saved in the primary matrix as correction values for each image.

Other possibilities to form correction values to eliminate the error factors due to eye motions is to correlate the help window information to the first image, or to use a device for supplemental measurement of eye movements, where the measured values are then converted into correction values for the vessel site under inclusion of the known geometric relationships; these corrected values are then saved in the described manner in the primary matrix as correction values.

The lighted measured field is used to reduce the light stress. In the case of a column-like measured window, after the definition of the measured window, the control unit can establish the coordinates of the lighted measurement field so that they cover the measured window, that is, the size of the measured field will be reduced to the size of the measured window. The advantage is a significant reduction in the light stress. During the measurement process, the lighted perimeter created by UBS can have a considerably limited diameter and lighting intensity or can even be switched off. The position of the perimeter lighting is automatically adjustable by means of the control unit or by means of the examiner. The use of the perimeter lighting for light provocation according to this invention will be described in greater detail below.

FIG. 4 presents the measured field in the shape of a circular field. In this case, the field aperture is formed as an iris aperture in the MBS. The lighted perimeter in FIG. 4 lights up the entire image field, but due to reduction in lamp current to the halogen lamp LQUB, it has a significantly attenuated lighting intensity. In a particular case it can also be useful to omit the modified, controllable lighting UBS and MBS in the retina camera and instead of that, the lighted field aperture of the retina camera is designed as a light-attenuating field aperture with fixed, central diameter as measured field. The image at the background of the eye might then appear as illustrated in FIG. 4.

The coordinates for geometry, position and lamp current to the perimeter lighting BSU and of the measured field lighting BSM are passed from the control unit SS to UBS and MBS. The coordinates for the geometry and position of the measured window and help window are received by the BM likewise from the control unit SS. The control unit receives the stated coordinates from a reference control matrix specified by the examiner or directly via dialog mode. In the latter case, the examiner controls the establishing of the described windows and fields and the brightness—preferably by using the computer 's mouse. In a known manner, mouse motion and actions can be converted by the control unit into control coordinates and due to the on-line action on the adjusting monitor, the controlled fields and windows can be monitored.

Depending on the capability of the modules and units of the device, several measured windows can be used by the examiner. The length and geometry of the lighted measured fields can then be adjusted to the measured windows. Another configuration of the measuring process according to this invention, is to establish several measuring windows whose geometry and position is the same as the lighted measured fields, and the measured windows in a defined time interval have only one defined geometry and position in the image field, but change their geometry and position in the image field in defined time intervals controlled by the control unit. All this, in order to examine different vessel sections one after the other without interruption of the examination. Now the same vessel sections can be checked as often as necessary once the measured windows and measured fields have been defined. This has the advantage that both the examination of slow time processes, as well as the examination of numerous vessel sections, is possible on-line within one examining period.

The method consists of various process groups:

0. Acquisition of patient data (default setting)

Reproducible setting of the background of the eye, in particular of vessel sections to be examined in the image field with the modified retina camera and the fixation device with the assistance of the control unit and of the adjustable monitor.

Establish the vessel sections to be examined on the adjustable monitor through definition of lighting and/or imaging windows (see below) by means of the control unit and of the manipulation unit and also use of the DE (mouse and keyboard) to form a control matrix S.

Measurement process to determine the vessel diameters along the vessel site and the time and formation of a primary data matrix P which establishes the relationships between the following primary data for each examination: P(IDU, IDP, A, DFDP, DFMi,DFPi, S, BZ, DZ, BF) and also graphic, on-line representation of selected interdependencies, preferably of the vessel diameter as a function of the time for all examined vessel sections Examination identification number IDU a patient code IDP, the examined eye A (right or left), a data sequence DFD with the to the vessel diameter D [sic]

data sequences for I additional measured quantities DFMi data sequences for I additional provocation events DFPi a control matrix S for the examination process a measurement beginning with the reference date BD and the reference time BZ an examined video image sequence BF Calculation of a corrected data matrix analysis process and formation of parameter matrices and display or output of parameters The abbreviations BZ, BD (reference date and reference time) mean the data and time when the evaluable images were taken. During on-line mode when image recording and measurement occur in the same time interval, the reference time BZ is equal to the actual system time SZ. The system time or system date means the current time or the current date. The relative time RZ means a time difference.

The primary data set of the control matrix S establishes the reference to the following quantities:

1. Sensitivity (magnification setting)
2. Fixation coordinates (x, y, coordinates, lamp current, inner/outer fixation)
3. Poor vision value
4. Lighted measured field coordinates (height, width, location in the image field, lamp current at the start time)
5. Lighted perimeter coordinates (diameter, location in the image field, lamp current, light manipulator state) at the start time
6. Reference value: time and data at start time (BZ, BD)
7. Tape ID when using optional recorder control
8. Time code of the start image or filename of the start image For the primary data sequence of vessel diameter, the primary data set contains the vessel diameter D as a function of the following quantities: D=F( 1. Diameter,
2. Current position of vessel diameter in the measured window (coordinates)
3. Current position of the measured window in the image field
4. Current correction coordinates from the help window(s) or additional measuring unit to determine the eye motions,
5. Relative time at beginning of measurement process RZ
6. Location-corrected position of the vessel middle in the object space belonging to the vessel diameter)

FIGS. 12 and 13 illustrate the diameter and the relative time RZ and the pixel location or scan site. The scan site is a different representation of the current position of the vessel diameter, but it can be computed from the data of this primary data sequence on vessel diameter.

Primary data matrix of a manipulation matrix:
Event values
Relative time
Primary data sequence of a measured data matrix (general):
Measured value
Relative time The sequence of an examination is described schematically in FIG. 5. Related measurement, control and analysis data within a temporal cohesive examination time interval with uninterrupted relative time and only one reference time and one reference date at relative time point=0 are called the "examination." Every examination has a unique identification number that relates the examinations to the examined image sequence, the patient and the measurement, control and analysis data via P. Several examinations on a patient's vessel can be carried out in one sitting.

The examination begins with the assignment of the new IDU and the identification of the patient (default values). The input of patient data, its editing and storage in the database and the data model for the general data on the patient proceed according to known methods and will not be detailed here. It is important to the invention merely that there will be a data relation of measurement, control and analysis data unambiguously to one particular patient. Once the default values have been taken, the vessel sections to be examined are adjusted to the image field of the adjustable monitor and the needed control parameters for the background of the eye are adjusted to the vessel sections to be examined and window positions are set by the control unit and by the examiner, who can implement and settings on the modified retina camera and verify them by means of keyboard and mouse on the adjustable video display. The setting must take place so that the background of the eye can be seen with the particular vessel sections sufficiently sharp and at high contrast on the adjustable monitor. The windows (to be described below) must be properly arranged to the examined vessel sections and the device pupilla must be centered precisely to the pupilla of the eye.

In the case of a repeat examination, all light-side windows and image-side windows (see below) will already have their default data saved and will be visible on the adjustable monitor. In this case, a reference examination will be selected by the examiner whose control matrix will be picked up as reference matrix. The adjusted parameters (control data) specified by the control unit for the repeat conditions are taken from the reference matrix and set as defaults. The reference matrix can set the settings needed for repeat conditions by using an already completed examination which is selected by the examiner. On the dialog monitor (PC-monitor) an image with the vessel and window position will be displayed for the examiner on the adjustable monitor for reference measurement. Due to the default setting of fixation coordinates for the reference measurement, the examiner need only make the setting between device and eye so that the device pupilla are cleanly fixed on the eye pupilla. The focus setting of the image will usually not be needed, since the poor vision from the reference examination will be known from the reference matrix and the focus setting is an automatic default via the control coordinates bsr. Resetting of image focus and fixation or [of?] window positions will still be possible by manual means and can be corrected in the control matrix according to the current values. After completion of the setting, the measurement process can begin, e.g., by using the mouse.

In the event that no repeat measurement is to be conducted, the examiner will select one of the default reference matrices to implement the corresponding default settings. Procedurally, defaults are provided to the examiner for various examination programs and can be saved in a reference matrix, which can be called up by the examiner to ensure that the same examination conditions are used.

In addition to the setting between device and eye, the examiner will use the fixing unit to adjust the vessel sections to be examined (movement of the fixing mark by using mouse or keyboard) to within the display field of the adjustable monitor and also adjust the image focus. Now if the windows are not set up as defaults, in the next step the window positions (see above) will be adjusted according to the examination program on the adjustable monitor, preferably with the mouse, and the measurement process to record the primary data will be started. Preferably at the moment when the measuring process is started, the new, current set parameters on the control unit for this examination will be saved in the control matrix for this examination, while preferably at this moment also a fundus image with window positions will be recorded as a control image for the measurement settings used in this examination. At the same time, this is also the first evaluable image of the image sequence of b=n images (b=1) and the reference value for the time point and data when the examination was begun (BZ, BD). During the measurement process, the examiner can correct the fixation coordinates or the settings on the device and eye pupilla and can terminate the measurement process at any particular point in time. The background of the eye, location of the window and vessel sections can be monitored in parallel on the adjustable monitor. Preferably the vessel diameter for each vessel will be recorded as a function of time, on-line on the dialog monitor. This setting will take place either by use of standard defaults and the settings will be saved according to generally known principles for saving the data model characteristic for the patient.

Figure 5:
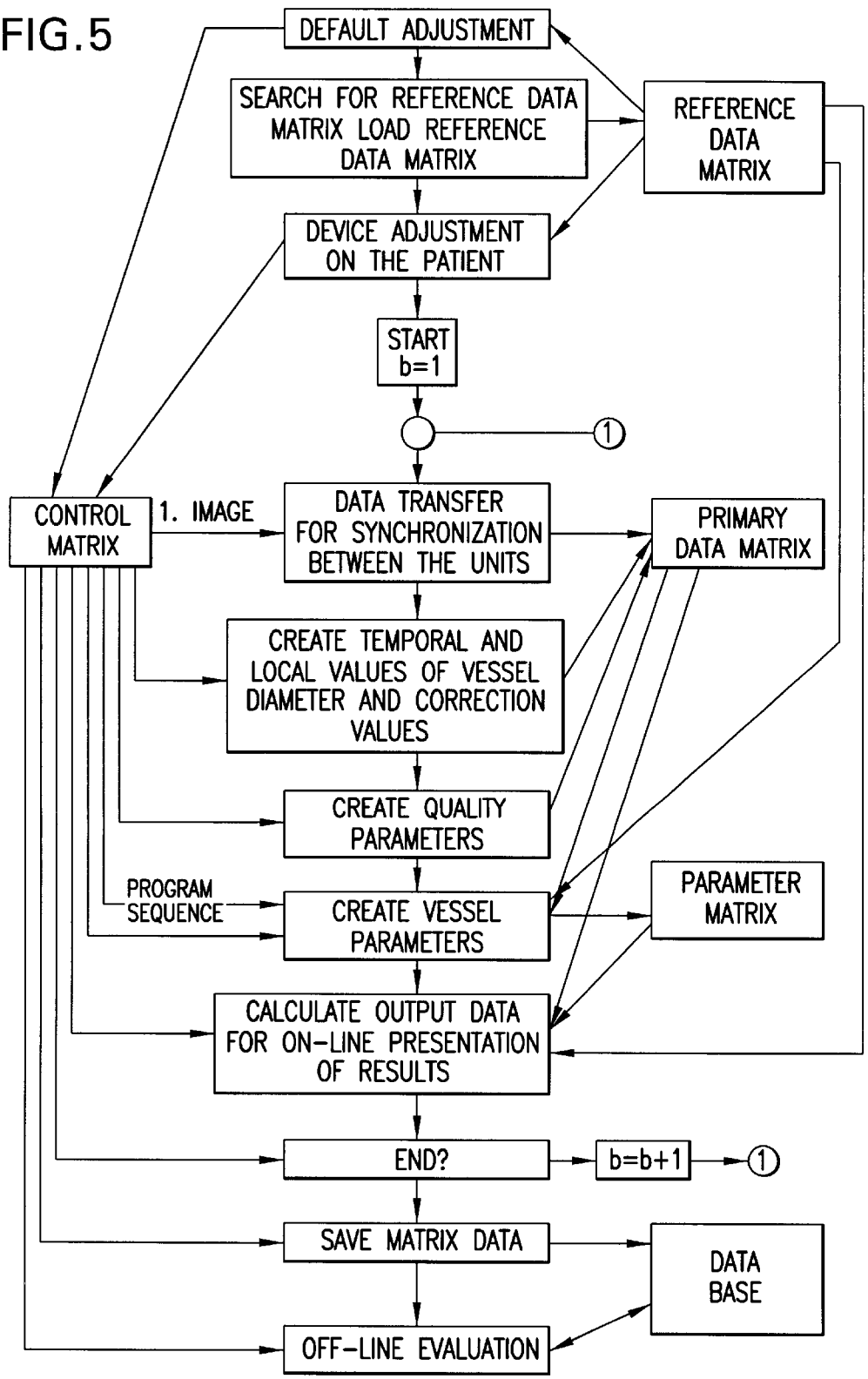

FIG. 5 explains the process sequence by using a block diagram. The description of the invented image and signal processing in the measuring and help windows makes use of only one example of one window, since the procedure is analogous when using several measuring windows.

All windows are processed by the diameter module DM (FIG. 1); the vessel located in the measured window will be output with its vessel diameter (corrected for slant position), the vessel middle position in the measured window, and the average slant position of the vessel with respect to the window, and then saved as a function of the image number of the sequence and the current position of the window in the image field will be saved in a primary data set. The vessel diameter can also be output from the diameter module without correction of the slant position. The recognized vessels in the current window will be allocated to each other based on their properties. Every diameter value of the data sequence on the vessel diameter in the primary data matrix will then be allocated to a reference 1 to I, one vessel after another, depending on how many differently classified vessels are detected. Software programs will subsequently be available to correct the classification, if necessary, after a visual inspection by the examiner after the examination, e.g., by inspection based on the saved image sequence. According to the invention and as already described, from the difference in vessel middle position and the slant position of the vessels, the position shift of the same vessels in the direction of the help window will be determined in the help window module as correction values for the small, arbitrary eye motions. From these correction values, from the imaging conditions, the current window coordinates, the fixation coordinates and the vessel middles in the image field—according to the invention, the object position of the vessel middles belonging to the vessel diameters (hereinafter called the vessel location)—will be computed relative to the reference point (foveola). The calculation will be related to the vessel and image and saved in the data sequence for vessel diameter in the primary data matrix (corrected object position of the vessel diameter in the fundus image). This will ensure that the vessel diameters will be comparable at the measured site, regardless of the adjusted object field and the exclusion of the influence of eye motions. A similar effect to eliminate small eye movements can be obtained, for example, by computing the image shift by means of correlation of the image information of the first help window against the current help window. The vessel slant positions will then be determined with respect to each other by correlation from neighboring rows of pixels. Another possibility is to measure the viewing motions in parallel during the measuring process. The changes in viewing direction with respect to a reference image, e.g., the first image, can then be used to correct the influence of eye motions at the measured site, instead of the correction values computed from the help windows.

The diameter module according to this invention represents a fast algorithm which will recognize vessel edges in the line signals of the windows, interpolate the photometric concentrations in the vessel edges, compute the slant position of the vessel edges, allocate the correct vessel edges to each other, determine the vessel diameter between the photometric edge concentrations, corrected for slant position, and compute the vessel middle position in the window.

Special measuring units are used to measure the blood pressure. The measuring unit for periodic pressure measurement MS1 features a computer interface that starts and stops the measuring process by means of control signals from the control unit SS. The determined blood pressure data are allocated by the control unit to the primary data matrix with proper time and image associations. The measuring unit MS2 consists of an EKG unit that supplies the R-peak of the EKG to the control unit via a computer interface, and from there the data is saved in the primary data set, allocated to the data sets correctly with regard to image and time. Preferably MS1 and MS2 will always be included in the measurement process, since by means of the R-peak the pulsation analysis will be simplified, and secondly, the blood pressure represents an important parameter affecting the vessel diameter, whose additional recording will eliminate sources of error. The additional measured quantities need not be recorded in parallel.

Additional measuring systems (MS3) can also be useful. One example of additional measurements is to determine the respiratory gas by means of respiratory gas analysis or to measure the suctorial pressure as a combination of measurements of local and temporal vessel diameter with the intraocular pressure increase by means of suctorial methods.

Furthermore, it is possible to use provocation devices MP to induce certain states for corresponding examinations. The respiratory gas provocation device MP1 features preferably a respiratory path for free respiration and an additional respiratory path for exhalation, which can be reverse switched. The oxygen and CO2-percentage in respiration air is measured periodically sufficiently close to the mouthpiece and sent to the control unit SS for recording in the primary data matrix correctly for image and time. By using control signals from the control unit, the respiratory gas routes are reversed under sequence control. Studies on the oxygen effect on the retina vessels are known, through measurement of single values and evaluations in a group comparison. With the invented device and the invented method, primarily the temporal and local response of the vessels to a provocation with oxygen, CO2 or carbogen in various concentrations in the respiratory air, or with oxygen in pure form, will be of interest. For example, a provocation with 100% oxygen preferably over 5 minutes is a preferred method for functional diagnosis of the contraction of the vessel sections.

The provocation device for physical stress Mps consists of a set of hand-held weights and an acoustic signal generator. The weights are standardized to the body weight of the patient and after a signal they are taken by the patient in the hand and then extended horizontally out to the side until a second signal, after which the patient brings the weight back down. Both signals are generated acoustically by the PC output unit, and the control signal is supplied from the control unit. Depending on the sequence plan, this provocation occurs during, before or between measurements on the eye.

An additional combination provocation device is one of the known systems for increasing the intraocular pressure by using the suctorial disk (MP3).

Provocation devices can be set up in parallel, but can also be used individually.

Preferably according to the invention, a possible provocation can be created by means of the described device using the modified retina camera itself. To do this we use the perimeter lighting beam path for the provocation. By means of the control unit and the described units of the UBS (see FIG. 11), via the control coordinates bsu, during the measurement process, the lamp current, the light modulator, the geometry and position of the perimeter lighting will be varied at the background of the eye so that a continuous or temporary light stimulus will be produced at the defined site of the background of the eye under examination; the effect of this stimulus on the diameter of the vessel at another site of the fundus can be recorded locally and temporally. One possible design format could use a brightness-alternating lighting as a kind of flicker to measure other circulatory parameters, within a papilla-sized surface central to the foveola placed in the macula, in order to examine the vessel response of the vena temporalis superior in comparison to the vena temp. inferior. The advantage of this is that with the vessel diameter, the behavior of the microcirculation will be determined directly and not merely indirectly via the change in blood speed arising due to the change in diameter, for instance. The described combination is a simple method for functional diagnosis of the retina vessels and moreover also for the functional integrity of the nerve fibers.

The additional processing of measured results takes place preferably first through the formation of additional vessel signals, in which all vessel diameters are reduced to one-fourth and the squares are again divided into one-fourth and then saved in additional temporal columns of the primary data matrix for evaluation as speed-related diameter Ag(x, y,t) and as flow-related diameter Qg(x,y,t), all correct according to vessel, location, time and image. These steps make possible a significant expansion of the validity of the invention, since they directly describe the complex effect of vasoacative factors of the vessel diameter on the flow quantities of blood speed and blood flow. The inclusion of these parameters is optional.

The additional processing of measured results takes place preferably first through the formation of additional vessel signals, in which all vessel diameters are reduced to one-fourth and the squares are again divided into one-fourth and then saved in additional temporal columns of the primary data matrix for evaluation as speed-related diameter Ag(x, y,t) and as flow-related diameter Qg(x,y,t), all correct according to vessel, location, time and image. These steps make possible a significant expansion of the validity of the invention, since they directly describe the complex effect of vasoacative factors of the vessel diameter on the flow quantities of blood speed and blood flow. The inclusion of these parameters is optional. [this paragraph is repeated in the original]

A distinction is made between on-line evaluation and off-line evaluation. The control of on-line evaluation takes place by the control unit SS according to defaults or user-defined settings. The off-line evaluation takes place by menu selection of the interesting vessel sections and signals, and by selecting the evaluation method and the parameters in a known manner.

The evalaution method offered to the examiner in this example for forming of parameters is combined into blocks in FIG. 5. The basis for this selection are the vessel, measurement and provocation signals saved temporarily or permanently in the primary data matrix in their local and temporal relationship. The following description is provided only for an evaluation of a vessel section and only for the vessel diameter Dg as vessel signal, since it will be analogous for the other vessel sections or vessel signals (Ag, Qg) (g denotes the vessel association to the vessel diameter).

By means of data masks, the analysis data will be read out from the primary data mask, correct in time, location and vessel, and sent to a state of the art filter for spectral and/or local filtering according to the purpose of the evaluation. The method of local frequency analysis determines the power spectrum, detects significant, local frequencies Fo and determines the association of phase positions Po to the infeed data stream either as a function of a time interval adjusted in the filter, as a time-dependent spectral parameter, or as a complex spectral parameter. The block for temporal frequency analysis determines the power spectrum of the selected signal sequence, detects significant frequencies Ft, determines their power Lt and phase position Pt and saves these determined spectral parameters I in the associated parameter matrices. From the determined spectral powers, the parameters VAPU are determined as a quotient of vasomotion and pulsation, PPU as a quotient of provocation response to the pulsation, and PVA as the quotient of the provocation response to the vasomotion, PUB as the quotient of the first order blood pressure wave to the pulsation, which are allocated to one of the parameter matrixes according to the data mask or the filter.

Phase differences between specified measured sections are computed and when the vessel sections are cohesive, the wave speeds are computed from the associated path lengths. The method of pulsation analysis determines R-peaks triggered for the corresponding local section and a time-averaged pulsation signal as a function of the pulse phase by means of a pulsation period, which is saved as a pulsation signal in the parameter matrices. The peak values of the pulse signals are determined as separate parameters and saved.

The local analysis process group provides the significant maxima MaO and MiO of the data sequence pertaining to the location, its temporal interval TO and the associated peak values SO, the average value MWO, its scattering SMWO and the confidence interval MWOK for a specified static dependability and also the number of included images 'nb' and measurement site 'no'. The vessel paths belonging to a pixel form the basis for calculation of the average value.

The static time analysis process group provides the significant, temporal extreme values MAT and MOT of the data sequence, their time interval TT and the associated peak value ST, the average value MWT, its scattering SMWT and the confidence interval MWTK for a specified, static dependability and also the number of images 'nb' included in the average values and the measurement site 'no.' Depending on filter selection and parameters, additional parameters for vasomotion, pulsation and blood pressure are also determined in this manner.

The dynamic time analysis process group uses adaptive methods to estimate the value of a significant rise APROV (negative rises as well) from the temporal trend, and the significant beginning of the rise BT. By appropriate setting of the parameters of the data mask and of filter parameters, the total average values and associated scattering are determined and saved as complex, location- and time-independent parameters (KMW, KSMW) in the complex parameter matrix for the associated vessel sections.

The iterative evaluation methods going from one image to the next, are also iteratively constructed, so that they can be represented on the monitor windows for on-line evaluation and on-line presentation of the measured or evaluated results.

The cross-correlation process group uses the cross correlation factor to determine the parameters that describe the relationship between the vessel responses and the supplemental provocation and measured signals.

Time-dependent parameters are saved in the time-dependent parameter matrix; location-dependent parameters are saved in the location parameter matrix, and time-independent and location-independent parameters are saved in the complex parameter matrix.

The image sequence comparison process group forms the percentage differences in parameters from the same vessel sections and vessel locations (x, y) and time phases (t) from the parameter matrices of a selected image sequence with the current image sequence, and preferably also the associated confidence intervals. The reference image sequence can be operator-defined, but the former image sequence is the default. Only those parameters are compared which have a comparable control data matrix.

The time comparison process group forms the percentage temporal differences from parameters of the same vessel section of an image sequence and preferably also the associated confidence intervals, whereby the time section of the reference value can be operator-specified. The default for the reference value is the first time value of a parameter in the image sequence. The peak value of the provocation responses is determined as additional comparison parameter for Regulative Region RB; the provocation-induced maximum is determined as a comparison parameter for upper regulative reserve and the minimum is determined as URR—Lower Regulative Reserve.

Figure 6:
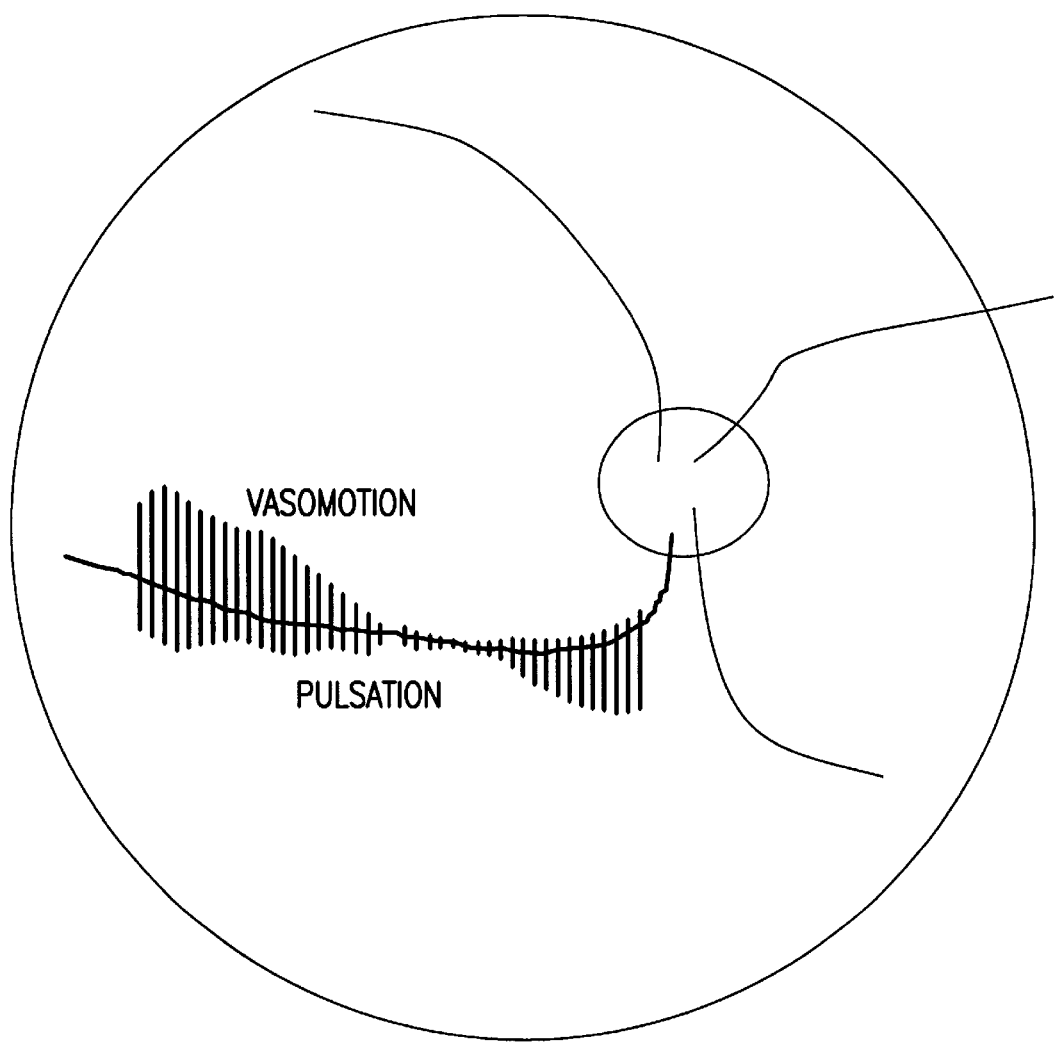
Figure 7:
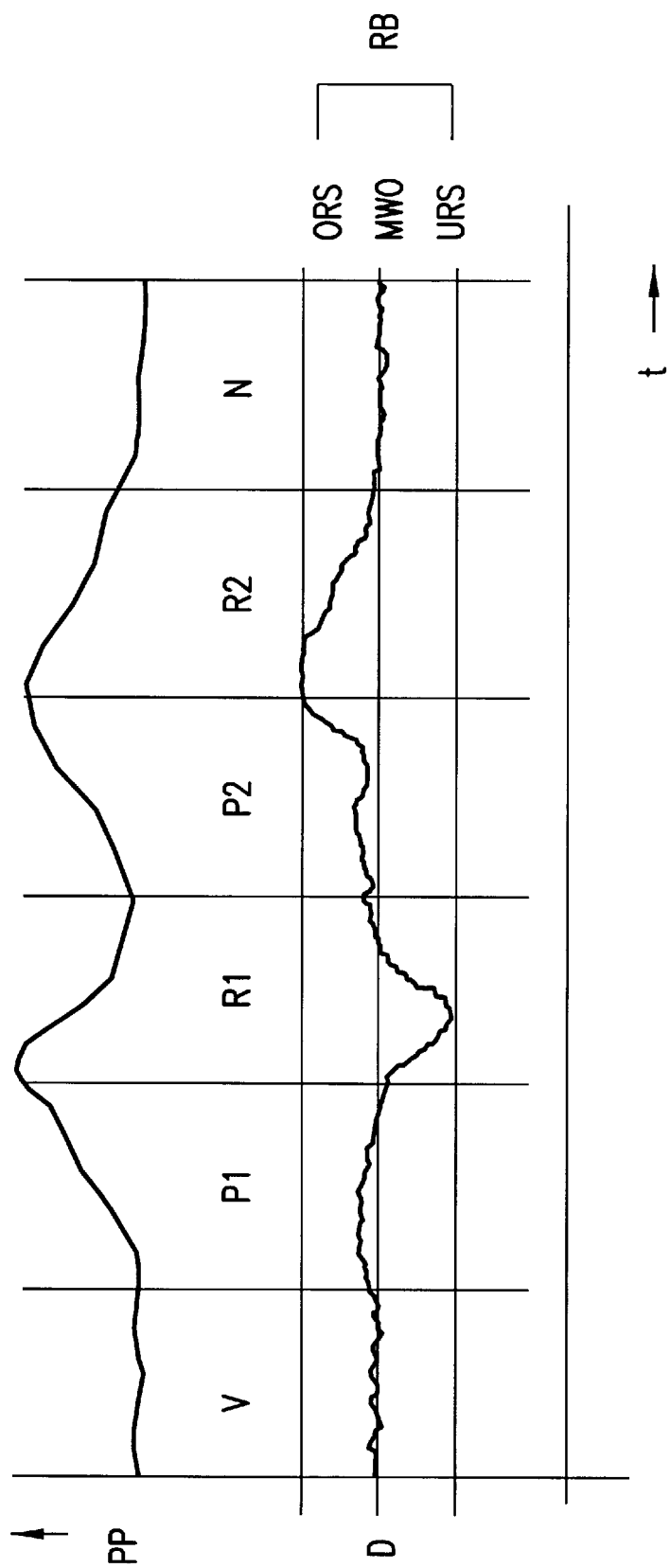

FIGS. 6 to 7 explain the presentation methods. The results according to this invention, will be displayed with the following presentation method on monitor images either in parallel or in sequence. The functional images presentation group presents the parameters or measured value as images corresponding to the vessel locations, or as central graphics as shown in FIG. 6. The measured values, parameters or comparison quantities are sufficiently differentiable visually as perpendicular or horizontal bars compared to the dashed profile of vessel location. Various parameters are indicated by color coding. These functional images appear on a gray background with the fundus images documented at the beginning of each image sequence; analogous to the measured values, they are first converted into the coordinates of the object plane. The presentation method can also be structured on image field coordinates, and in this case it is not the vessel sites, but rather the vessel middles that are used. As an example, FIG. 6 shows the parameter Lt of pulsation plotted against Lt of vasomotion, and the values for pulsation are presented beneath and the values for vasomotion are presented above the vessel site. At first glance, those vessel regions are discernible which are rigid, exhibiting neither pulsation nor vasomotion, or those vessel sections that still respond flexibly to the pulse, but for which vasomotion is no longer detectable. In the same way, the metabolic or the provocation parameters, the regulative regions, the regulative reserve or other parameters can also be displayed. Through appropriate control it is also possible to collect different vessel sections from different image sequences into one function image, e.g., vessel sections that were recorded in sequence.

The time display presentation group makes possible a display of value sequences from the different levels of the evaluation process as a function of time, and the type of display can be user-defined.

The location display presentation group allows the display of value sequences from the different levels of the evaluation process as a function of the vessel path, whereby the display can be user-defined. The vessel path is computed as a slant-position-corrected distance to the vessel middle (vessel distance) or the vessel position (vessel path) and saved in the primary matrix. The vessel distance is therefore the image of the vessel path in the object plane.

Preferably all the stated evaluation methods should be available for equipment systems to be used for research purposes. But it makes no difference to the invention how many of the methods are actually available or employed for the particular application. Even a simple presentation of numeric values for evaluation by the physician, would allow qualitatively new insight compared to the state of the art, even though significantly constrained. The graphic display of data on the primary data matrix, the formation of characteristic values and their graphic presentation is incomparably better with regard to content and effectiveness, than the mere presentation of primary data, since the new relationships obtained according to the invention, cannot be readily discerned in their fullness and validity by mere numeric values.

The invention also makes possible an on-line presentation of the results. The on-line output operations are controlled by the control unit according to the sequence plan. The presentation of results is a default setting or user-defined settings with the on-line evaluation method. The adjustable monitor M1 continuously displays the image of the background of the eye and the current window positions. At the beginning of the measurement process, the first image of the background of the eye is fully digitized and saved according to the control data matrix for the image sequence and is available in a monitor image window. At the beginning of the measurement process, the vessel diameters of the detected vessels are output as control signals in an additional monitor window as a function of time, in parallel with the provocation signals—and optionally—output together with the additionally determined measured signals unprocessed or after filtering.

In additional monitor windows, iteratively determined parameters of the evaluation method can be displayed on-line with priority of the measurement process and of the other named monitor windows.

The control unit SS takes over the entire process control of measurement and evaluation, interface control for the exchange of control and measuring signals with the units, control signal formation, synchronization between the units and in particular, dialog mode with the input and output units. The control unit also administers the database system, in which the created control matrix, parameter matrix and primary data matrix or perhaps the image sequences are saved and administered under one image sequence identifier and examination code IDU. The image sequence code consists of a primary key generated by the database management system for the control unit and is intended for identification of the image sequence BF and for incremented image coding 'b'. The images belonging to an examination are designated as an image sequence. If autonomous video sources are used, then the control unit takes the image sequence frequency of the video source as a clocked series and assigns a time basis to the image sequence. In the case of controllable video sources, the control unit supplies the timing signal for the image sequence frequency or for transfer of the next image. The image code then consists of the image sequence code and a sequence number as identifier for the current image. In addition, the control matrix holds the identifier of the memory medium where the evaluated image sequence is recorded parallel for evaluation.

In addition to the other process steps, the measurement method is characterized in that according to the clinical problem and the used provocation method, functional time segments are formed as a kind of measurement and pause phase. The program sequence consists of measurement phases and pause phases and these can be defined by the user with respect to the number of phases z, number of images per phase bz, image repetition frequency fb, image evaluation frequency fa. Preferably the default settings will be established for the standard procedure, which consists of preliminary phase, provocation phase 1, response phase 1, provocation phase 2, response phase 2 and post-phase, and one pause phase can be provided between each of the phases, but are defaults for the example with 0 images. The pause phases mean a continuance of the time basis in the measurement sequence without image evaluation, associated with an automatic blanking of the lighting and attenuation of the fixation lighting for recovery by the patient. Preferably these time regions are included by the mask and the filters for standard evaluation.

In the case of several measured windows not evaluable in one image sequence, within the functional phase there is one sequence control for sequential polling of the various measured windows and the variation of measured windows in the scan regions belonging to the various measured windows. Preferably the inner polling cycle consists of a series of different measured windows, and the other cycle is determined by the stochastically defined change in position of the measured window in the scan region.

According to the invention, a help program of the control unit SS acts as follows: When defining the measured windows and the examination program, on the basis of the desired temporal and local resolution and the measured times, this help program computes the expected bounds for significantly detectable changes. In this case, when used with repeat measurements, it determines the estimated systematic errors representative for a patient group from the database, or it refers back to a patient group representative of the parameters saved in the parameter set, and these parameter sets are updated due to each new examination and supplied to the database for these calculations. When making the adjustments, the examiner can make an optimum compromise between patient stress and the expected information gain, depending on the priorities in the clinical problem at hand, and adjust the measuring properties of the system to the patient and the particular problem.

In the sample design, according to this invention a combination of two provocation systems is used which, on the one hand, effect opposing responses (dilation/contraction) and thus indicate a regulative region, and on the other hand, make it possible to detect and calculate the effect of blood pressure on the metabolic regulation. Thus the pulsations and blood pressure waves can be evaluated under different points of view. New parameters that pulsatory and vasomotor activities in the single measurement times to the provoked changes blood pressure changes due to physical stress in relation to set, indicate diagnostic significant and are with the described method randomly definable and presentable [sic].

FIG. 5 presents an overview of the group of combined process steps for the cycle of one image.

The default setting makes possible a change in the manufacturer default settings and the user-specified programming of the measurement, evaluation and presentation method, including the default setting of parameters for control, for setting the scope of dialog mode for adjusting the measured window, the help window and the measured field for adapting the measurement station to the individual requirements of examiner and patient. Various default settings can be saved and updated subsequently on a menu. At this point the default settings will be made for measurement and pause phases in the method, and the user can specify the type of presentation of results on the monitor and on the measurement protocol and the collection of patient data The adjustment method makes possible in dialog mode the setting of the parameters not handled by manufacturer defaults, the initializing of the device and program units. The updating of defaults will be offered to the user and they can be modified at this time. A sequence of comparison images can be defined. They are fetched from the database and kept available in the working memory. Optionally parameters or the entire control matrix of the comparison image sequence can be used as a default. In the case of repeat measurements, the setting of all preceding examinations will be offered as a default, and automated, precision comparison conditions, including the reproducibility of the measured site, are implemented. A lacking of comparable examining conditions, in particular the measured site, is an important deficiency of the state of the art method, especially from the view of the large biological variability. After setting the examining device to the patient 's eye, there appears an object field section imaged on the image field (corresponding to the default setting of the fixation device) which can be observed on the control monitor. The default setting of the measured and help windows and of the measured field is superimposed on the fundus image on the control monitor M1. By moving the mouse, the fixation device can be adjusted to change the imaged object field from the background of the eye; the location or geometry of the measured window, the help window and the measured field can be changed, likewise the default compensation for poor vision.

When starting the measurement, an image sequence code will be generated which is saved by the control matrix with the first image. The sequence control first calls up control programs to drive the apparatus units via the interfaces, to poll the measured data and to save it in the control or primary data matrix appropriate to image and time, to generate and transmit control signals. When starting the measurement, the perimeter lighting will be reduced to a default value, usually shut off, and the measured field lighting will be increased to the default value.

Due to the sequence control, one image after the other is moved into the image manipulator, saved with the identity code, displayed with the measured and help windows on the control monitor, and parallel with this, the windows of the image are digitized and evaluated in the described process steps, and the results are saved in the primary data matrix. According to the sequence planning, the window coordinates in each image will be changed by driving the image manipulator, and perhaps also the measured field coordinates will be changed by driving of the imaging system.

In this design example, preferably the quotient of the number of the detected vessels to the line number of the measured window is used as a quality parameter QUALI. This quality identifier is used to control the measured field brightness to minimize the light stress. According to the invention, from the intermediate results the algorithms can derive additional parameters for window evaluation which, as quality parameters, detect the image contrast, the SNR, the current photometric resolution, etc., which can be used to optimize the optical filter position by tipping in the beam path, to optimize the light stress and to optimize the CCD camera properties. The adaptive control of the CCD camera in this invention using measurement criteria makes possible an adjustment to the high, biologically induced variability of image quality. The use of quality identifiers is not required, however.

It is not required, but the forming of additional vessel signals will provide a significant expansion of the value of the intention, when the squares and 4th powers of the vessel diameter can be determined, as already described above, and saved in the primary data matrix for use in determination of parameters. This process group can also include the determination of additional plethysmographic vessel signals and determine their changes plethysmographically and allow a comparison with the diameter vessel signals.

With the next process group, the formation of parameters, the selected evaluation method and associated masks and filter parameters are called up in sequence according to the defaults and adjusted. By means of the adjustable masks and filters, data is compiled from the primary data matrix, or the parameter matrices of the current image sequence, and perhaps also from the reference image sequence, then processed and used to determine parameters with the current evaluation method and then saved in the parameter matrices.

The process block of on-line presentation refers to the primary data and parameter matrices, perhaps also to the control matrices by means of adjustable masks, in order to compute the output data from the selected presentation method, and to pass it to the control unit SS for output in the next cycle.

After working through the specified number of images of the sequence program, the on-line measurement process is ended, the matrices of the current image sequence saved; if necessary, documentation programs are called up from a menu, the measured value protocols and the presentation of results are prepared on line and sent to the printer.

Next, access is enabled to an off-line evaluation, the default evaluation program is automatically executed to form the parameters and associated presentation programs, or a menu-driven, individual formation of parameters is possible together with preparation and output of suitable results. The integration of the database manager also makes it possible to include and compare the result from any other image sequences saved in the database.

One important innovation of the invention over the state of the art is the possibility to determine vessel diameters on a continuous basis, on-line, simultaneous with the location along the vessel, and to analyze them. Beyond this qualitative step, the invention also makes it possible to reduce the measuring error and thus the detection limit for changes in vessel diameters by nearly one power of ten and thus to penetrate into the realm of biologically induced changes in vessel diameter and the influence of blood pressure.

Figure 8:
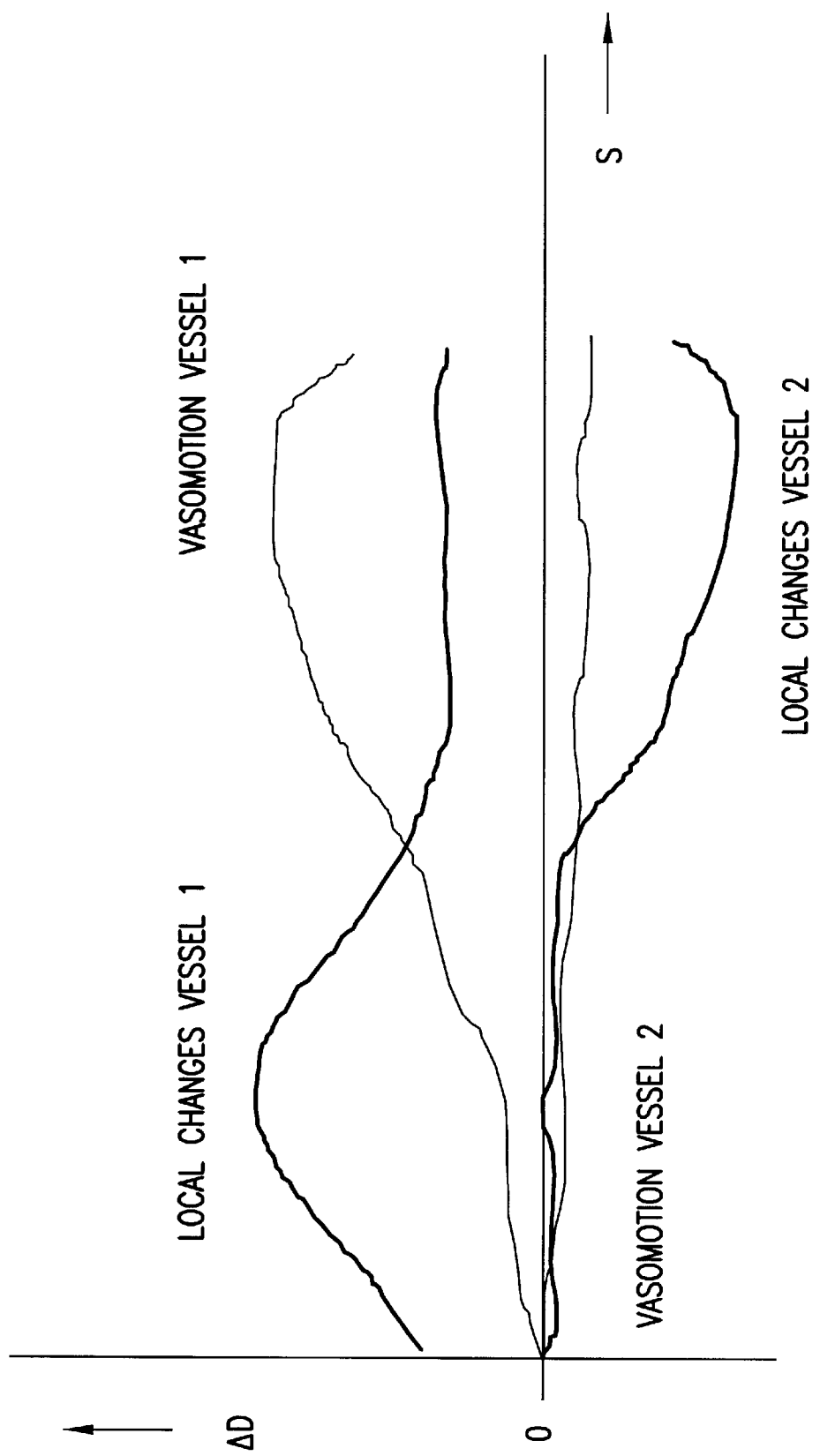

FIGS. 7, 8 and 9 show three examples for measured results that demonstrate the capability of the invention.

FIG. 6 presents a functional chart with a comparative representation of vasomotion peak values and pulsation peak values. The representation for the spectral power of pulsation frequency and vasomotion frequency would look similar. The values for the parameters are plotted in the direction of the y-axis with the vessel profile as abscissa—positive for the vasomotion and negative for the pulsation. The chart background is the fundus image, so that the parameters and their measurement sites can again be allocated to the background of the eye. Based on this image, the advantage of this presentation of results is evident—it allows a fast determination of the problem and an evaluation.

Immobile vessel regions with very small or absent vasomotions and pulsations are indicative of sclerotic vessel regions. Vessel regions with absent vasomotion but present pulsations, mean that this region still responds flexibly to the blood pressure, but exhibits no activity of the vessel musculature. Vasomotions and pulsations can not only be detected, but can also be locally resolved and quantified.

The more vessel sections are included in the measurements, the more comprehensive will the evaluation of the fundus situation be. The potential of the invention to measure not only several vessels simultaneously in one measured window, that is, to take measurements in parallel, but rather also to determine vessels in different quadrants quasi-parallel with several measured windows in one sitting, is another significant advantage.

FIG. 7 presents the changes in the average vessel diameter D measured across the vessel section plotted against the time and measurement phases, together with the average upper arm blood pressure PP. The advantage of the invented, continuous recording of the vessel diameter under provocation, and also the relationship to the blood pressure and the invented combination of the types of provocation used in the example, is clearly demonstrated here. In the preliminary phase, the initial value of the vessel diameter is measured, that is to say, its operating point under the current blood pressure conditions. The physical load leads to an increase in blood pressure and accordingly to a passive expansion of the vessels, which leads to the response of a bottleneck (auto-regulation) due to the elongation. The quotients computed as parameters, e.g., from changes or increases in blood pressure and vessel diameter, are a measure for the flexibility of the vessel wall (provocation phase P1) and for the contraction response in the second maximum (response phase 1). Whereas in provocation phase P2 due to rebreathing, a rising blood pressure is attained as in phase P1 and the beginning of contracting auto-regulation is still just barely discernible, in the second part of P2 the metabolic regulation begins as a response to the rebreathing. The maximum illustrates the reserve for regulation dilatation and can again be related to the magnitude of the provocation, e.g., to the changes or increases (not illustrated in this diagram) in the CO2 or O2-content of the rebreathed air.

The diagram shows the regulative region, the upper and lower regulative reserve, which can also be computed as parameters. The regulation capacity of the vessels can now be evaluated for the very first time.

The outstanding advantage consists in the new possibility for evaluation of the current vessel diameter. The anatomical scattering of the retinal branch vessel diameter is 15 to 20% within an individual and this allows recognition of a constricted or dilated position only in case of large changes and is very unreliable. Due to the invented measuring station, a constricted or dilated position can be determined much more sensitively and dependably based on the upper and lower regulatory reserves. The absolute value of the vessel diameter now has hardly any significance at all. Thus the source of error of the individual imaging of the eye is eliminated, provided that changes in the optical properties of the eye between the examinations can be neglected.

Thus the technical requirements are established for a functional diagnosis of the microcirculation and also for a screening method to evaluate vasoactive medications and to evaluate the degree of sclerosis as a risk factor. Since all vessels ascertained by the measured window are measured and their parameters displayed, the diagram of FIG. 8 can also serve as a comparative representation of a branched artery and branched vein, which allows even more far-reaching conclusions.

The diagram in FIG. 7 is suitable in particular for on-line presentation as a display in a window of the monitor M2. In this regard it would also make sense to display the oxygen and CO2 content of the respiratory air in parallel.

FIG. 8 shows another example for a comparative presentation of results on the behavior of a branched vessel at two different times, e.g., before and after therapy. On the abscissa we see the actual path along the vessel run and on the ordinate, the spectral vasomotion power and the local change in vessel section for the current image sequence (solid line) and the reference image sequence whose vessel diameter was used as reference value at the coordinate origin. Compared to the reference time, this vessel has expanded, particularly in the first half of the section. But precisely in this region the vasomotions missing at the reference time are still quite normal, while the vasomotions in the originally contracted vessel region are re-established.

In the sample design explained above, various solutions for the invented device and method were combined with each other whose effect on the measured result differs significantly from the state of the art, since they allow a comprehensive analysis of changes in vessel diameter using previously unknown reproducibility and detection limits that had been presumed heretofore to be impossible. However, not all of the listed methods for parameter formation will be needed for every medical problem. In some cases, a determination of one parameter will suffice.

The application of the invention makes it possible to form only one, or even all of the parameters, and to record and evaluate only local and/or the temporal profile of vessel diameter. Even simple designs of the invention have a surprising effect and a satisfactory reproducibility or detection limit for changes in diameter which are sufficient for numerous clinical problem constellations.

For example, the automatic reproduction of the measured site due to the invented fixation device can be omitted, when inaccuracies pertaining to the allocation of the vessel sections to each other can be omitted. Likewise, the help window can be omitted if local inaccuracies in measured value allocation are allowed, which due to eye motions, lead to a more or less powerful and precise floating average value formation across the local dependence associated with a reduction in the local resolution. A simple design consists, e.g., in a retina camera with known lighting and imaging beam path which is not modified at all. A common red-free filter can be used. Additional provocation and measuring systems and the parallel recording of the TV image can also be omitted. Only one measuring window with a scan region is placed in the image, or one measured window that fully covers the entire scan region. In this case, the determination and presentation of parameters can occur as in the first design example, but only the temporal or local profile, or only the averaged pulsation period can be evaluated visually. This presumes that in the non-scanning measured window, the vessel diameter is determined locally resolved and not as an average value for the measured window as in the scanning measured window. With an apparatus of this type surprising effects can be seen, such as vasomotion and pulsation, therapeutic of functionally provoked changes can also be viewed, however, not by any means with the detection limit and resolution as in the previous design example.

Likewise, it is possible to use a flash image sequence with defined time intervals instead of the camera and to evaluate off-line or on-line in the described manner. The disadvantage then consists in the absent temporal resolution. The sequence controller then has to configure the image recording so that in the image sequence, the influence of pulsation or vasomotions will be eliminated, e.g., by randomizing. The invested application off-line makes possible an evaluation of all vessel sections measurable in the image, in which the scan motion sectionally and sequentially covers the entire image field, or the scan motion of the measured window is controlled (per this invention) so that the vessel middle is always located in the middle of the measured window and the scan motion in both directions of the vessel run is continued for as long as the vessel is measurable. In this case, a ring-like help window whose diameter is greater than that of the papilla is sufficient. At the locations of discernible vessels, this help window generates small measured windows whose scan motions adaptively follow the vessel run.

Another simple design format is the plethysmographic spectral analysis for conjunctiva vessels, which represents another simple design example. As imaging system, an illuminating beam path with a red-barrier bandpass filter of 540 nm with 100 nm bandwidth and an imaging beam path is used; this can be, for example, a slit lamp and in the imaging beam path is a single-surface photoelectric sensor tuned to the spectral transmission of the filter. Outlet connected to the sensor there is an amplifier and a frequency analyzer that outputs the power spectrum. With this imaging system, a larger vessel in the microcirculation can be imaged on the photoelectric measured surface of the sensor. This imaging must occur such that the vessel diameter in the vessel section is entirely covered by the measured surface. The frequency spectrum supplies the pulsation and vasomotion power whose values or whose quotient are displayed as parameters for clinical evaluation.

The design example can be expanded to other optically accessible regions merely by use of an endoscope as imaging system, for example. Employment on fluorescence angiography imaging systems is also a possibility. In this regard it makes no difference for the invention whether conventional, optical systems or laser scanners are used as imaging system. But the use of laser scanners has the disadvantage that the attainable reproducibility and local resolution or accuracy of local measured value allocation is reduced significantly.

Furthermore, it makes no difference to the invention whether the measured surface covers the entire scan region and the evaluation of the measured surface reflects the local profile of the vessel diameter, or in a favorable manner, using minimal computational effort as described in the design example, if it consists of a narrow measured window that produces an average value for the vessel diameter in the measured window and determines the local profile in sequence by means of a scan motion of the measured window.

It is of no importance to the invention how the computational hardware is configured. The computational hardware merely specifies the compromise of temporal, local resolution, number and surface area of measured windows, and the performance capability of the on-line presentation of results. One particularly favorable design format for the invention is to configure a ring-shaped measurement field congruent to a ring-shaped measuring surface. The ring-shaped measuring surface can also be composed of several strip-like measuring surfaces, preferably with mutually overlapping ends, composed into a polygonal shaped ring. But this design of the invention requires a greater computational effort for the on-line capability.

In addition, it is of no relevance to the invention whether the back- calculation to the object plane occurs with the proper imaging scale or is stated in relative units. The precise local allocation of measured values and of measured locations to each other within the image or object plane is decisive in this case.

REFERENCE LIST

| | |
|---|---|
| O | Object |
| BS | Imaging system |
| FI | Fixation device |
| BE | Image receiver |
| BM | Image manipulator |
| EP | Units for presentation of the results, e.g., TV monitor |
| ES | Controllable video recorder |
| SS | Control unit |
| BV | Evaluation unit |
| DE | Keyboard |
| MP | Manipulation unit |
| MS | Measuring unit |
| HS | Main beam path |
| US | Perimeter illuminated beam path |
| UBS | Perimeter lighting system |
| BO | Lighted lens |
| BLS | Lighted beam path |
| FS | Fixation beam path |
| FAS | Outer fixation beam path |
| FIS | Inner fixation beam path |

-continued

| | |
|---|---|
| SE | Mirror unit |
| S1 ... S4 | Mirrors |
| OL | Ophthalmoscope lens |
| HOS | Optical system |
| MBS | Measured field lighting system |
| y | Fixation marks |
| y', y" | Images of the fixation marks |
| FME | Fixation mark unit |
| FOS | Fixation optical system |
| AA | optical unit |
| MSB | Measured illuminated beam path |
| MBÖ | Opening aperture |
| MBÖ' | Pupilla of the opening aperture |
| FMB | Filter |
| MBL 1 | Lens system 1 |
| MBL 2 | Lens system 2 |
| Y" | Images of a plane congruent to the background of the eye |
| MBF | Field aperture (image produced at the background of the eye) |
| SMBF | Adjusting unit for field aperture |
| SMBÖ | Adjusting unit for aperture diaphragm (control of brightness) |
| LQMB | Light source |
| SVMB | Controllable power supply to the light source |
| UBS | Measured illuminating beam path |
| UBÖ | Opening aperture |
| UBÖ' | Pupilla of the opening aperture |
| FUB | Filter |
| UBL 1 | Lens system 1 |
| UBL 2 | Lens system 2 |
| UBF | Field aperture (image produced at the background of the eye) |
| SUBF | Adjusting unit for field aperture |
| SUBÖ | Adjusting unit for aperture diaphragm |
| LQUB | Controllable power supply to the light source |
| LM | Light modulator |
| SLMUB | Adjusting unit for light modulator |
| p, p', p" | Pupilla locations |
| G1, G2 | End points of the scan region or measured surface in the vessel direction |
| BZ | Reference time |
| BD | Reference date |
| IDU | Identification number of the examiner |
| RZ | Relative time |

What is claimed is:

1. Device for the investigation of biological vessels, preferably of retinal vessels, in which at least one vessel section is present as an electronic image or as a series of electronic images, which is supplied from a photoelectric receiving device to an evaluation unit, whereby the evaluation unit contains an image manipulation unit (BM) for section by section digitizing or blanking of at least one measured window in the image created by the photoelectric receiving unit and for identification of the image and of the position of the measured window in the image; a control unit (SS) to create the image identifier and the measured window coordinates which describe the position and geometry of the measured window in the image; image-processing or signal-processing computing and storage units (BV) and output units (EP) for display of the image and/or display of measured values and/or of measured results, whereby the arrangement contains means by which the component of the measuring window contains in the direction of the expanse of the vessel at least so many pixel positions that are detected that the inclined position of the vessel in relation to the measuring direction can be determined and the vessel diameter can be resolved in a manner selected from the group consisting of in terms of location by at least two vessel diameter values of directly neighboring vessel segments of the same vessel, and in terms of time by at least two vessel diameter values per the same vessel segment between different images.

2. Device according to claim 1, characterized in that the geometry and/or the position of the measured window in the image and its orientation in the image are controllable.

3. Device according to claim 1, characterized in that at least one measured window is of a strip design.

4. Device according to claim 3, characterized in that means are provided for switching between horizontal and vertical position.

5. Device according to claim 1, characterized in that the components of the measured surface transverse to the vessel run amount to 10-times that of the expected vessel diameter and that at least 6 pixels of a line or column are located simultaneously on the component of the measured window located transverse to the vessel run.

6. Device according to claim 1, characterized in that at least one measuring window is designed as a ring strip or as a ring polygonal section using rectangular strips preferably mutually overlapping at the corner.

7. Device according to claim 5, characterized in that for application to the background of the eye, the inner diameter of the ring or polygon section is at least as large as the diameter of the papilla.

8. Device according to claim 1, characterized in that means are provided so that at least a number of pixel layers can be adjusted as corresponds to the component of the measured window in the direction of the vessel run, so that the maximum and minimum changes in vessel diameter of the quasi-periodic, local changes in vessel diameter will be ascertained.

9. Device according to claim 1, characterized in that means are provided for manual or automatic definition of a scan region within which the measured window changes its position stochastically or systematically from one image to the next, and that the scan region is preferably at least 1.5 mm in size.

10. Device according to claim 1, characterized in that means are provided for changing the radius of the circular or polygon-shaped measured surface within a manually or automatically defined scan region, from one image to the next, and that the scan region is preferably at least 1.5 mm in size.

11. Device according to claim 1, characterized in that the photoelectric receiving device is an imaging system with at least one image receiver, and one illuminating beam path is provided and that in the plane of the illuminated beam path congruent to the object plane there is a partly transparent aperture for definition of a measured region, said aperture consists of a fully transparent measured field region and a partly transparent perimeter region.

12. Device according to claim 1, characterized in that the intensity of an illuminating light and/or the position of the partly transparent aperture can be controlled in the plane congruent to the object field by means of measured field coordinates.

13. Device according to claim 1, characterized in that the photoelectric receiving device is an imaging system with at least one receiver and has at least one illuminated beam path for perimeter lighting, and that at least one additional illuminated beam path is located in the lighted, main beam path which creates an additional, lighted measured field in the object plane, which is superimposed on a primary light, or separates the object field, from a lighting point of view, geometrically into the measured field and the perimeter field formed by the main beam path.

14. Device according to claim 13, characterized in that servoelements are provided that use measured field coordinates independently of the main lighting or perimeter lighting, to control the position and/or geometry and/or intensity and/or spectral properties and that the measured field coordinates are created by the control unit and transmitted to the servoelements.

15. Device according to claim 1, characterized in that means are provided with which the measured window and the measured surface can be set up and moved confocal.

16. Device according to claim 1, characterized in that means are provided in the image manipulation unit so that in addition to the measured window, at least one help window is created in the image with a fixed position to the image, which detects movements and/or positions of object edges in the help window and saves them as correction coordinates in a primary matrix and/or are used on an image for immediate correction of movements of the vessel middle positions in the image field during one image sequence.

17. Device according to claim 16, characterized in that the help window is identical to the measured window in the first image at the beginning of measurement.

18. Device according to claim 16, characterized in that the help window is designed as a strip-like window and at the beginning of measurement stands perpendicular and central to the measured window.

19. Device according to claim 1, characterized in that means are provided for spectral tuning of the lighting and/or imaging light, said means having a bandpass character with steep edges and properties such that they have the smallest possible tolerance for medium wavelength and bandwidth and reside in a series

| Middle wavelength | Bandwidth (Half-value width) |
| --- | --- |
| 540 nm | 100 nm |
| 533 nm | 70 nm |
| 563 nm | 50 nm |
| 574 nm | 10 nm |

20. Device according to claim 1, characterized in that for application on the eye, an inner and/or outer fixation device with fixation servoelements is provided, which unambiguously describes—in defined fixation coordinates—the angle between the optical axis of the eye and of the imaging system, performs the fixation setting and that means are provided to control and/or determine these fixation coordinates and also to transfer the fixation coordinates between control unit and fixation devices.

21. Device according to claim 1, characterized in that the fixation coordinates of the inner and of the outer fixation device are identical for the mutually overlapping fixation regions and that means are provided to control and/or determine these fixation coordinates and also to transmit the fixation coordinates between control unit and fixation devices.

22. Device according to claim 20, characterized in that refraction servoelements are provided with which the fixation marks can be focused for the patient one time before beginning the sequence of measured values and that through suitable refraction measurements, the adjusted fixation refraction value for focussing is measured and transmitted to the control unit.

23. Device according to claim 20, characterized in that an aperture is positioned in the illuminating beam path or behind the outer fixation mark so that it covers at least the foveola of the eye to be examined, or in the case of outer fixation, it covers the neighboring eye.

24. Device according to claim 1, characterized in that means are provided that stochastically change the brightness or shape of the fixation marks.

25. Device according to claim 1, characterized in that means are provided with which in the case of rough or indefinitely determined, relative shifts in position, an acoustical signal and/or a temporarily differently modulated brightness modulation or shape control of the fixation mark will occur.

26. Device according to claim 1, characterized in that means are provided with which at the beginning of the measurement, the entire image with measured window is saved as a control for the measured site.

27. Device according claim 1, characterized in that that means are provided which recognize vessel edges in the digitized measured windows, interpolate the photometric edge concentrations for all discernible vessel edges in the measured windows, perform a vessel edge allocation by unambiguously assigning the determined values to individual vessel sections, calculate the slant position of the vessels to the measured window from the local shift in middle or edge position of mutually cohesive vessel sections of the same image, determine the vessel diameter from the slant-position-corrected distance of mutually cohesive photometric edge concentrations, determine the vessel middle position in the image for each vessel diameter, and save the determined vessel diameter and vessel middle positions in a primary data set for each recognized vessel, image by image.

28. Device according to claim 25, characterized in that means are provided for vessel allocation which take the current, recognized vessel and assign it unambiguously to the recognized vessels of the preceding images or define a new vessel and expand the primary data set by a new vessel.

29. Device according to claim 1 characterized in that means are provided for calculation and image-by-image storage of the average brightness in the present measured windows or measured window regions as the vessel signals in the primary data set describing the vessel diameter.

30. Device according to claim 28, characterized in that means are provided which determine the average brightness in the center as the vessel brightness, in the edge region as edge brightness, and in the vessel perimeter as perimeter brightness and save the data appropriate to each vessel in the primary data set.

31. Device according to claim 1, characterized in that additional measuring means (MS) are provided whose measured signals are allocated to and saved in the primary data set or control data set correctly for each image or image sequence.

32. Device according to claim 30, characterized in that the measuring means perform a quasi-continuous acquisition of blood pressure signals and/or intraocular pressure signals and/or EKG-signals and/or pulse signals.

33. Device according to claim 30, characterized in that the measuring means can be controlled by the control unit.

34. Device according to claim 1, characterized in that manipulation systems (MP) are provided which cause a defined change in biological parameters on the microcirculation and/or the metabolism and that the associated, provocation signals are saved in the primary data set allocated appropriately to each image.

35. Device according to claim 33, characterized in that the biological parameters are intraocular pressure and/or respiratory gas composition and/or physical stress and/or temperature and/or light stimulus.

36. Device according to claim 34, characterized in that the manipulations systems can be controlled by the control unit.

37. Device according to claim 1, characterized in that,
an on-line memory unit ES is provided for image sequences
the image manipulator supplies each image with an image identifier and measured sequence code
the image identifier and measured sequence code are created by the control signal unit and passed to the image manipulator and that the image identifier of the particular, evaluated image is saved in each primary data set and the measured sequence code is saved in the associated control data set.

38. Device according to claim 1, characterized in that units are provided for spectral analysis of the vessel signals and measured signals and for display and storage of the results of the spectral analysis.

39. Device according to claim 1, characterized in that, means are provided for optional time and space filtering of the vessel signals and that filtered vessel signals are sent to the unit for spectral analysis.

40. Method for the examination of biologic vessels, preferably of retinal vessels, in which at least one vessel section is present as an electronic image or as a sequence of electronic images which is sent from a photoelectric receiver to an evaluation unit, characterized in that vessel signals are created that described the vessel diameter of at least one vessel section by use of temporal and/or spatial resolution;
in a manner selected from the group consisting of by combining at least two vessel diameters of directly neighboring vessel segments and by combining at least two vessel diameters of the same vessel segment of images different in terms of time, to form one vessel signal.

41. Method according to claim 40, characterized in that in the acquisition of an image with a photoelectric receiving device, by means of the automatic or manual setting of at least one measured window, and by setting of a measured range and by means of multiple movement of the measured window within the measured range, measured data are created which represent at least one vessel diameter with spatial and temporal resolution.

42. Method according to claim 40, characterized in that the time-variable measured data of the measured window are recorded, saved and processed.

43. Method according to claim 40, characterized in that,
in accordance with a task-specific structure plan, images of the image sequence are evaluated or created in the specified number and at the specified time interval,
this time interval is used as the time basis of the vessel signal and
vessel signal values—together with the vessel middle position and/or measured window coordinates and/or measured field coordinates—are allocated to each other in time and space for each evaluated image and saved in a primary data set.

44. Method according to claim 40, characterized in that the primary data sets of a measurement procedure are combined into a primary data matrix.

45. Method according to claim 40, characterized in that fixation and help window coordinates and/or scan regions and/or refraction value of the device for focusing the fixation mark are determined or formed which are not changed during a measuring process or during an image sequence and are allocated together with an identifier of the measuring process in a control data set for the primary data matrix of an image sequence.

46. Method according to claim 40, characterized in that in the help window and/or in the main window, the local shift of at least one characteristic image pattern in each evaluated image is determined in proper coordinates for the first image of a measurement process or for each preceding image and is saved with chronological accuracy as a help window correction value in the primary data set.

47. Method according to claim 46, characterized in that the characteristic image pattern is the actual vessel to be analyzed and the position of the vessel pattern is the position of the middle of the vessel.

48. Method according to claim 40, characterized in that the corrected vessel middle positions of the particular vessel diameter value are calculated from the fixation and/or measured window coordinates and/or the help window correction values with respect to a defined reference point in the image plane, and are saved with chronological accuracy in the primary data matrix.

49. Method according to claim 40, characterized in that the location-dependent vessel signals are frequency-analyzed before and/or after filtering as a function of the location and/or of the time; the frequency spectrum and phase position are graphically displayed and/or subsequent local and/or chronological frequency parameters are determined and saved in a complex identifier matrix.

50. Method according to claim 49, characterized in that as identifiers, one or more of the quantities of vasomotion frequency, bandwidth, power and phase-position, pulsation frequency, bandwidth, power and phase position, and also frequency, phase position, bandwidth and power of additional detectable frequencies are used.

51. Method according to claim 40, characterized in that additional measured signals that describe parameters affecting the vessel diameter, are assigned to at least one value in the control data set of the image sequence or are assigned chronologically to the vessel signals in the primary data set.

52. Method according to claim 51, characterized in that blood pressure parameters and/or the intraocular pressure and/or pulse and/or heart phase are used as parameter factors.

53. Method according to claim 40, characterized in that additional manipulation signals that describe the artificially created parameters affecting the vessel diameter, are resolved in time (at least) and allocated to the vessel signals in the primary data set.

54. Method according to claim 40, characterized in that from the vessel signals, additional vessel signals are formed in which the square of the values and/or the 4th power of the values is formed and saved in the primary data sets.

55. Method according to claim 40, characterized in that characteristic quantities are formed from the vessel, measured and/or manipulation signals.

56. Method according to claim 40, characterized in that vessel signals and/or measured signals and/or manipulation signals and/or parameters are superimposed on the vessel image, or are allocated to or displayed as time-profiles and/or as local two- or three-dimensional profiles as functional diagnostic images and/or are presented numerically or graphically as complex, whole values independent of time and location.

57. Method according to claim 40, characterized in that after and/or before temporal and/or local filtering of the vessel signals, from the corrected vessel middle positions of the vessel signals, local regions and time regions are formed that include at least one value and that from the vessel signals within the local regions and time regions, location-dependent time parameters are determined and are saved and displayed in a time parameter matrix for the particular, defined time and location regions, and/or are output superimposed on the original image as a function of the corrected vessel middle position as a functional-diagnostic image for the defined time region and location region.

58. Method according to claim 57, characterized in that the location-dependent time parameters are maximum and minimum values with respect to time and/or with respect to the temporal average values from the vessel signals, their temporal scattering and confidence intervals and/or the roots of the temporal average value from the squares of the vessel diameter, the associated scattering and confidence intervals and/or the ¼ power of the temporal average value across the 4th power of the vessel diameter and their scatterings and confidence intervals.

59. Method according to claim 57, characterized in that heart pulse regions are defined and that for each local region—by means of EKG-triggered signal average of the vessel signal or diameter—the average value, scattering and confidence interval within the heart pulse regions are formed and saved.

60. Method according to claim 59, characterized in that pulse parameters such as the pulse phase position, the maximum pulse value and the minimum pulse value are determined from the pulse profile and saved.

61. Method according to claim 57, characterized in that the signal filters processing the vessel signals are bandpass filters with outlet connected, floating average value formation that select or smooth the heart pulsation and/or heart vasomotion and/or blood pressure waves of 1st and/or 2nd order and/or the respiratory frequency, and/or smooth foreign signals and/or interferences.

62. Method according to claim 40, characterized in that before and/or after a default local and/or temporal filtering of the vessel signals, temporal regions and vessel regions are formed that include at least one value and that from the local vessel runs within the time regions and vessel regions, time-dependent local parameters are determined and are saved in a local parameter matrix for the defined location and time region and are output graphically as a function of time for the particular vessel region.

63. Method according to claim 62, characterized in that the time-dependent local parameters are the maximum and minimum values and/or the local average value of the vessel signal, whose scattering and confidence intervals are formed, and in the local parameter matrix as a function of the time and/or that the roots of the local average value from the squares of the vessel diameter, the associated scattering and confidence intervals and/or the ¼ power of the local average value across the 4th power of the vessel diameter and its scattering and confidence intervals.

64. Method according to claim 62, characterized in that heart pulse ranges are specified and that for each time region, the average value, scattering and confidence interval within the heart pulse regions are formed as average values with respect to location by means of EKG-triggered signal averaging of the vessel signal or diameter and are saved and displayed.

65. Method according to claim 64, characterized in that pulse characteristic parameters are determined from the pulse profile and saved and that the pulse parameters are the local average pulse phase position, the local average pulse maximum value and the local average pulse minimum value.

66. Method according to claim 40, characterized in that complex parameters are formed from the local parameter matrix and/or time parameter matrix or primary data matrix and are saved in a time-independent and location-independent complex parameter matrix correctly with respect to vessel, time region and local region and output.

67. Method according to claim 66, characterized in that maximum and minimum value, temporal and local average and its scattering are formed from the local and/or time parameters and/or vessel signals, e.g., from the vessel diameter and/or that the root of the temporal and local average and its scattering is formed from the squares of the particular vessel signals and/or that the ¼ power of the temporal and local average and its scattering, is formed from the 4th power of the values of the vessel signals, e.g., the vessel diameter.

68. Method according to claim 40, characterized in that quotients and/or differences and/or percentage differences are formed as derived parameters from the location, time and complex parameters among and with each other, which are each saved in the location parameter matrices or time or complex parameter matrices and are displayed or output accordingly as location, temporal or complex parameters.

69. Method according to claim 68, characterized in that as derived parameters, the pulse peak values and vasomotion peak values are brought into a relation with each other and/or that the frequency powers and/or the frequencies or phase position of pulse and vasomotion are related as new parameters and/or the peak values of the vessel diameter are brought into a relationship relative to the local or temporal or complex average value.

70. Method according to claim 40, characterized in that dynamic parameters are determined by signal analysis from the time profiles of the provoked or pathologically or therapeutically induced signal changes and are saved in the complex parameter matrix or in the time parameter matrix as dynamic parameters correctly with respect to vessel and/or location and are displayed.

71. Method according to claim 70, characterized in that the dead time, the decay and rise time constants of the direct response and of the reactive phase of the vessel sections to oxygen inhalation and/or to isometric stress and/or to change in the intraocular pressure and/or to light stimulus are determined by local resolution or as a response of a vessel region.

72. Method according to claim 40, characterized in that different vessels and/or vessel regions of a vessel are analyzed simultaneously, or simultaneously or sequentially within the same image sequence and the intervals of the corrected vessel middle positions are converted into comparable vessel length units and are displayed graphically in two or three dimensions for a comparison of their vessel signals or parameters.

73. Method according to claim 40, characterized in that parameters are formed that pertain to local and/or temporal and/or complex changes in a vessel and/or vessel section with respect to a reference vessel or a vessel section.

74. Method according to claim 40, characterized in that simultaneous measurements of at least two associated vessel sections or vessel regions are carried out and that the phase difference of mutually associated vessel sections of a vessel region and/or different vessel regions is determined and/or in addition, the flow paths between the vessel sections are determined and from phase difference and flow paths, the pulse wave rate is determined and output.

75. Method according to claim 40, characterized in that the temporal and local relationships between the corrected and/or uncorrected vessel signals and the provocation signals and/or supplemental measured signals and/or parameters are displayed graphically in two and/or three dimensions.

76. Method according to claim 40, characterized in that the parameters are determined anew for each new, evaluated image and output in one of the graphic or text displays.

77. Method according to claim 40, characterized in that a control parameter calculates the positioning uncertainty with each image iteratively as the scattering of help window correction values in both directions and/or continuously displays the values and the final value of the measurement sequence is saved in the control parameter set with the measured value sequence.

78. Method according to claim 76, characterized in that for a particular value due to the parameter of positioning uncertainty, due to the sequence control an acoustical signal and/or a prominent visual signal is introduced to the brightness or shape of the fixation mark by means of the sequence control.

79. Method according to claim 77, characterized in that the acoustical or visual signal becomes greater with increasing positioning uncertainty.

80. Method according to claim 40, characterized in that the image quality parameters in the primary data set are saved in correct chronology for each evaluated image.

81. Method according to claim 79, characterized in that the image quality parameters are used for canceling of vessel signal values, provided the value is outside of a default value range.

82. Method according to claim 70, characterized in that the image quality parameters are used to provide each measured value with a weighting factor which has a particular value in the case of very good image quality, and has the value zero for very poor quality, and has a graduated value for values of image quality lying in between, and that these weighting factors are used in the determination of average values for greater weighting of more dependable measured values and for attenuating or elimination of more uncertain measured values.

83. Method according to claim 40, characterized in that the first image of a measurement sequence is saved in its entirety and allocated to the control set of the measured sequence, and the measured window and help window and/or the scan regions in the image are identified with associated naming of the measured sequence and are graphically displayed or output as a local measured image.

84. Method according to claim 40, characterized in that during repeat measurements, the measured and/or help window coordinates and shape and/or fixation coordinates and/or measured field coordinates and/or scan regions are automatically set to their defaults by the sequence controller or are displayed for manual setting, and that the local measured image of the preceding measurement process is presented.

85. Method according to claim 40, characterized in that the measured signals or parameters are presented graphically in their temporal or local profile or on-line with their determination.

86. Method according to claim 84, characterized in that the average value and a confidence interval of the average value are determined iteratively and displayed as current value with each evaluated image, or are displayed graphically with the measured signal.

87. Method according to claim 40, characterized in that the measured window and/or measured field within the specified scan region is moved between various images or within one image stochastically or by pixels or sections in the direction of vessel run.

88. Method according to claim 40, characterized in that various clinical standard questions are assigned to various progress controls for the measurement process, that the preparation of the image sequence or evaluation of an existing image sequence takes place for a measured process in the quantity of images and/or in the temporal image spacing and/or is controlled automatically with a specified control data set, that this data is saved as control parameter in a control data set and that the measurement process is terminated when the confidence interval falls below a default value.

89. Method according to claim 87, characterized in that the reproducibility desired by the examiner is requested in dialog mode and from the default control values, the needed number of measured values and/or examining time is computed.

90. Method according to claim 87, characterized in that an image sequence of at least 10 images/s over at least 10 s or at least 1 image/s over at least 120 s or at least 0.2 images/s over at least 600 s is recorded and/or evaluated.

91. Method according to claim 87, characterized in that an image sequence of at least 10 images is recorded and/or evaluated stochastically distributed over at least 5 minutes.

92. Method according to claim 40, characterized in that the sequence controller controls the lighting of the measured field and switches to full intensity only during the measurement and otherwise uses reduced values.

93. Method according to claim 40, characterized in that the lighting intensity in the measured field is regulated by the sequence control during the measurements and as control quantities, default values for the image quality parameters are used and the minimum light intensity needed for the specified image quality parameters is always used.

* * * * *